US010947587B2

(12) United States Patent
Geng et al.

(10) Patent No.: US 10,947,587 B2
(45) Date of Patent: Mar. 16, 2021

(54) SINGLE-CELL FORENSIC SHORT TANDEM REPEAT TYPING WITHIN MICROFLUIDIC DROPLETS

(71) Applicant: The Regents of the University of California, Oakland, CA (US)

(72) Inventors: Tao Geng, Richland, WA (US); Richard Novak, Brookline, MA (US); Richard A. Mathies, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 546 days.

(21) Appl. No.: 15/031,140

(22) PCT Filed: Nov. 5, 2014

(86) PCT No.: PCT/US2014/064171
§ 371 (c)(1),
(2) Date: Apr. 21, 2016

(87) PCT Pub. No.: WO2015/069798
PCT Pub. Date: May 14, 2015

(65) Prior Publication Data
US 2016/0265043 A1 Sep. 15, 2016

Related U.S. Application Data

(60) Provisional application No. 61/900,269, filed on Nov. 5, 2013, provisional application No. 61/970,282, filed on Mar. 25, 2014.

(51) Int. Cl.
*C12Q 1/68* (2018.01)
*C12Q 1/6858* (2018.01)

(52) U.S. Cl.
CPC .................. *C12Q 1/6858* (2013.01)

(58) Field of Classification Search
CPC .............. C12Q 1/6858; C12Q 2563/159
See application file for complete search history.

(56) References Cited

U.S. PATENT DOCUMENTS

| 6,480,791 | B1 | 11/2002 | Strathmann | |
| 8,148,068 | B2 | 4/2012 | Brenner | |
| 2003/0186272 | A1 | 10/2003 | Dau et al. | |
| 2005/0079510 | A1* | 4/2005 | Berka | B01L 3/502707 506/16 |
| 2005/0287572 | A1 | 12/2005 | Mathies et al. | |
| 2007/0020617 | A1* | 1/2007 | Trnovsky | C12Q 1/68 435/5 |
| 2009/0317797 | A1* | 12/2009 | Paterlini | C12Q 1/6883 435/6.11 |
| 2010/0248237 | A1* | 9/2010 | Froehlich | C12Q 1/6834 435/6.14 |
| 2010/0285975 | A1 | 11/2010 | Mathies et al. | |
| 2013/0085082 | A1* | 4/2013 | Vermeesch | C12Q 1/6886 506/9 |

FOREIGN PATENT DOCUMENTS

| WO | 2008150432 A1 | 12/2008 | |
| WO | WO2013123125 | * 8/2013 | .............. C12Q 1/68 |
| WO | WO2014028537 | * 2/2014 | .............. C12P 19/34 |

OTHER PUBLICATIONS

Butler JM. Short tandem repeat typing technologies used in human identity testing. Biotechniques. Oct. 2007; 43(4): ii-v. Review.*
Perrott, Jimmy. Optimization and Improvement of Emulsion PCR for the Ion Torrent Next-Generation Sequencing Platform. (2011).*
Dressman D, Yan H, Traverso G, Kinzler KW, Vogelstein B. Transforming single DNA molecules into fluorescent magnetic particles for detection and enumeration of genetic variations. Proc Natl Acad Sci U S A. Jul. 22, 2003; 100(15):8817-22. Epub Jul. 11, 2003. (Year: 2003).*
Maricic T, Pääbo S. Optimization of 454 sequencing library preparation from small amounts of DNA permits sequence determination of both DNA strands. Biotechniques. Jan. 2009; 46(1):51-2, 54-7. (Year: 2009).*
Novak R, Zeng Y, Shuga J, Venugopalan G, Fletcher DA, Smith MT, Mathies RA. Single-cell multiplex gene detection and sequencing with microfluidically generated agarose emulsions. Angew Chem Int Ed Engl. Jan. 10, 2011; 50(2):390-5. (Year: 2011).*
Sanchez-García JF, Gallardo D, Ramírez L, Vidal F. Multiplex fluorescent analysis of four short tandem repeats for rapid haemophilia A molecular diagnosis. Thromb Haemost. Nov. 2005; 94(5):1099-103. (Year: 2005).*
Butler JM. Short tandem repeat typing technologies used in human identity testing. Biotechniques. Oct. 2007; 43(4): ii-v. Review. (Year: 2007).*
Geng et al. "Microchip Analyzer For Forensic Short Tandem Repeat Typing Of Single Cells," National Institute of Justice, Grant Report, Jun. 2013 (retrieved on Feb. 8, 2013), 40 pages. Retrieved from the Internet: http://nij.gov/publications/pages/publication-detail.aspx?.

(Continued)

*Primary Examiner* — Teresa E Strzelecka
*Assistant Examiner* — Olayinka A Oyeyemi
(74) *Attorney, Agent, or Firm* — Bret E. Field; Rudy J. Ng; Bozicevic, Field & Francis LLP

(57) ABSTRACT

A short tandem repeat (STR) typing method and system are developed for forensic identification of individual cells. Agarose-in-oil droplets are produced with a high frequency using a microfluidic droplet generator. Statistically dilute single cells, along with primer-functionalized microbeads, are randomly compartmentalized in the droplets. Massively parallel single-cell droplet PCR is performed to transfer replicas of desired STR targets from the single-cell genomic DNA onto a coencapsulated microbead. These DNA-conjugated beads are subsequently harvested and reamplified under statistically dilute conditions for conventional capillary electrophoresis STR fragment size analysis. The methods and systems described herein are valuable for the STR analysis of samples containing mixtures of cells/DNA from multiple contributors and for low concentration samples.

11 Claims, 17 Drawing Sheets
Specification includes a Sequence Listing.

(56) References Cited

OTHER PUBLICATIONS

Metzger et al. "Direct sequencing Of Haplotypes From Diploid Individuals Through A Modified Emulsion PCR-Based Single-Molecule Sequencing Approach," Mol. Ecol. Resour., Jan. 2013, vol. 13, No. 1, pp. 135-143.

Novak et al. "Single Cell Multiplex Gene Detection And Sequencing Using Microfluidically-Generated Agarose Emulsions," Angew. Chem. Int. Ed. Engl., Jan. 10, 2011, vol. 50, No. 2, pp. 390-395.

Zeng et al. "High-Performance Single Cell Genetic Analysis Using Microfluidic Emulsion Generator Arrays," Anal. Chem., Apr. 15, 2010, vol. 82, No. 8, pp. 3183-3190.

Bontoux et al. "Integrating whole transcriptome assays on a lab-on-a-chip for single cell gene profiling", Lab on a Chip, 2008, vol. 8, pp. 443-450.

Geng et al. "Microchip Analyzer For Forensic Short Tandem Repeat Typing Of Single Cells", National institute of Justice Grant Report, Jun. 2013 [retrieved on Feb. 8, 2013], 40 pages. Retrieved from the Internet: <URL: http://hij.gov/publications/pages/publication-detail.aspx?ncjnumber-247280>.

Geng et al. "Minimizing inhibition of PCR-STR typing using digital agarose droplet microfluidics", Forensic Science International: Genetics 14 (2015), pp. 203-209.

Hartmann et al. "Gene expression profiling of single cells on large-scale oligonucleotide arrays", Nucleic Acids Research, 2006, vol. 34, No. 21, e143, 11 pages.

Kurimoto et al. "An improved single-cell cDNA amplification method for efficient high-density oligonucleotide microarray analysis", Nucleic Acids Research, 2006, vol. 34, No. 5, e42, 17 pages.

Marcus et al. "Microfluidic Single-Cell mRNA Isolation and Analysis", Analytical Chemistry, vol. 78, No. 9, May 1, 2006, pp. 3084-3089.

Marguerat et al. "Next-generation sequencing: applications beyond genomes", Biochemical Society Transactions, vol. 36, Part 5, 2008, pp. 1091-1096.

McCloskey et al. "Encoding PCR Products with Batch-stamps and Barcodes", Biochem Genet. 2007, vol. 45, pp. 761-767.

Metzger et al. "Direct Sequencing Of Haplotypes From Diploid Individuals Through A Modified Emulsion PCR-Based Single-Molecule Sequencing Approach", Molecular Ecology Resources, Jan. 2013, vol. 13, No. 1, pp. 135-143.

Schepers et al. "Dissecting T cell lineage relationships by cellular barcoding", Journal of Experimental Medicine, vol. 205, Sep. 29, 2008, pp. 2309-2318.

* cited by examiner

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 1
ccctgggctc tgtaaagaa                                               19

<210> SEQ ID NO 2
<211> LENGTH: 24
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 2
atcagagctt aaactgggaa gctg                                         24

<210> SEQ ID NO 3
<211> LENGTH: 33
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 3
gccctagtgg atgataagaa taatcagtat gtg                               33
```

```
<210> SEQ ID NO 4
<211> LENGTH: 30
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 4
ggacagatga taaatacata ggatggatgg                                      30

<210> SEQ ID NO 5
<211> LENGTH: 32
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 5
attgcaactt atatgtattt ttgtatttca tg                                   32

<210> SEQ ID NO 6
<211> LENGTH: 28
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 6
accaaattgt gttcatgagt atagtttc                                        28

<210> SEQ ID NO 7
<211> LENGTH: 21
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 7
gtgattccca ttggcctgtt c                                               21

<210> SEQ ID NO 8
<211> LENGTH: 22
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 8
attcctgtgg gctgaaaagc tc                                              22

<210> SEQ ID NO 9
<211> LENGTH: 19
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 9
actgcagtcc aatctgggt                                                  19

<210> SEQ ID NO 10
```

```
<211> LENGTH: 21
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 10
atgaaatcaa cagaggcttg c                                          21

<210> SEQ ID NO 11
<211> LENGTH: 22
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 11
atatgtgagt caattcccca ag                                         22

<210> SEQ ID NO 12
<211> LENGTH: 26
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 12
tgtattagtc aatgttctcc agagac                                     26

<210> SEQ ID NO 13
<211> LENGTH: 23
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 13
ggtgattttc ctctttggta tcc                                        23

<210> SEQ ID NO 14
<211> LENGTH: 26
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 14
agccacagtt tacaacattt gtatct                                     26

<210> SEQ ID NO 15
<211> LENGTH: 21
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 15
atgttggtca ggctgactat g                                          21

<210> SEQ ID NO 16
<211> LENGTH: 24
```

```
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 16
gattccacat ttatcctcat tgac                                          24

<210> SEQ ID NO 17
<211> LENGTH: 26
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 17
attacagaag tctgggatgt ggagga                                        26

<210> SEQ ID NO 18
<211> LENGTH: 19
<212> TYPE: DNA
<213> ORGANISM: Artificial Sequence
<220> FEATURE:
<223> OTHER INFORMATION: Primer used in the study of forensic short
      tandem repeat (STR) identification of single-cell genomic DNA

<400> SEQUENCE: 18
ggcagcccaa aaagacaga                                                19
```

US 10,947,587 B2

SINGLE-CELL FORENSIC SHORT TANDEM REPEAT TYPING WITHIN MICROFLUIDIC DROPLETS

CROSS-REFERENCE TO RELATED APPLICATION

This application is a U.S. national phase entry under 35 U.S.C. § 371 of International Application No. PCT/US2014/064171, filed Nov. 5, 2014, which claims benefit of U.S. Provisional Patent Application No. 61/900,269, filed 5 Nov. 2013, and titled "SINGLE-CELL FORENSIC SHORT TANDEM REPEAT TYPING WITHIN MICROFLUIDIC DROPLETS," and U.S. Provisional Patent Application No. 61/970,282, filed 25 Mar. 2014, and titled "SINGLE CELL FORENSIC SHORT TANDEM REPEAT TYPING WITHIN MICROFLUIDIC DROPLETS," which are incorporated by reference herein in their entireties and for all purposes.

STATEMENT OF GOVERNMENT SUPPORT

This invention was made with government support under Grant Number 2009-DN-BX-K180 awarded by the United States Department of Justice Office of Justice. The government has certain rights in the invention.

BACKGROUND

Technical Field

The present disclosure relates to methods and systems for single-cell forensic short tandem repeat (STR) typing within microfluidic droplets for forensic identification.

Description of Related Art

Short tandem repeat (STR) typing, the gold standard for human forensic identification, relies upon the collection of homogeneous, light-quality and concentrated genetic samples from a crime scene. However, biological evidence samples often present mixtures of contributions (cells/cells or cells/DNA) from multiple individuals at relatively low concentrations. These complex biological samples generate mixed genotypes, presenting challenges in interpreting the results, especially when there are more than two contributors. Another difficulty arises when the perpetrator cells are much rarer than the victim cells, resulting in preferential amplification of the victim DNA. A variety of strategies have been developed to separate different cell populations prior to analysis to reduce the challenges in mixture interpretation, including differential extraction, filtration, fluorescence-activated cell sorting and microchip-based separation. More recently, laser capture microdissection and micromanipulation have been employed to analyze samples at the single-cell level. However, these methods are limited due to their complexity, low efficiency, low throughput, high risk of sample cross-contamination and/or lack of universality.

SUMMARY

One aspect involves a method fur forensic short tandem repeat (STR) identification of single-cell genomic DNA by forming aqueous polymer gel droplets in a hydrophobic oil such that a significant fraction of the gel droplets contain only one cell and only one primer-functionalized bead; isolating the gel droplets from the hydrophobic oil; immersing the encapsulated gel droplets in a cell lysis buffer, such that the cell lysis buffer dissolves the cellular protein and membrane and releases the genomic DNA into the polymer gel; washing the get droplets to remove the cell lysis buffer; soaking the get droplets in a PCR solution including forward and reverse primers, such that at least one forward or reverse primer is functionally identical to a forward or reverse primer on the primer-functionalized bead; performing emulsion oil PCR amplification of STR fragments, such that the emulsion oil PCR includes transferring replicas of desired STR targets from the single-cell genomic DNA onto the coencapsulated beads; isolating the beads; statistically diluting the isolated beads followed by performance of a secondary PCR amplification of the STR fragments; and determining the tandem repeat length of the STR fragments.

In some embodiments, the aqueous polymer gel is an agarose gel. In some embodiments, the aqueous polymer get is a gel at room temperature and molten at a temperature above room temperature. In various embodiments, the gel allows diffusion of enzymes and small reagents but does not allow released cellular DNA to leave the get droplet.

In some embodiments, determining the tandem repeat length includes performing a size-based separation method. The STR length may be determined by capillary electrophoresis. In some embodiments, the droplets are made with a microfluidic generator.

Another aspect involves a kit including a microfluidic droplet generator for generating gel droplets derived from an aqueous polymer gel, each droplet containing only one cell and one primer-functionalized bead; a PCR solution including forward and reverse primers, such that at least one forward or reverse primer is functionally identical to a forward or reverse primer on the primer functionalized bead; a centrifuge for isolating beads after emulsion oil PCR amplification of STR fragments; a DNA analyzer for determining tandem repeat length of STR fragments after secondary PCR amplification; and instructions for performing the method.

Another aspect involves a method for profiling single-cell short tandem repeat DNA sequences by performing multiplex amplification of short tandem repeat DNA sequences from individual cells in microfluidic droplets and determining the tandem repeat length. In various embodiments, performing the amplification includes performing PCR. The length may be determined by size-based separation. In some embodiments, determining the length includes performing capillary electrophoresis. In some embodiments, the method includes compartmentalizing individual cells in polymer gel droplets, in such embodiments, the method may further include isolating genomic DNA from the individual cells in the polymer gel droplets.

Another aspect involves a method for profiling single-cell short tandem repeat (STR) DNA sequences by forming microfluidic droplets containing statistically dilute microbeads and single cells; performing multiplex emulsion oil amplification of the short tandem repeat sequences in the microfluidic droplets such as to bind the STR amplicons from single cells to individual microbeads; and isolating the individual microbeads and determining the tandem repeat length of the bead-bound amplicons. In some embodiments, performing the amplification includes performing PCR. In some embodiments, the length is determined by size-based separation. In some embodiments, determining the length includes performing capillary electrophoresis.

Another aspect includes a method of profiling single-cell short tandem repeat sequences by forming microfluidic droplets containing statistically dilute microbeads and single cells; performing multiplex emulsion oil amplification of the short tandem repeat sequences in the microfluidic droplets to link the STR amplicons from single cells to the microbeads;

isolating the individual microbeads and performing a secondary PCR amplification of the STR sequences bound to each isolated bead to produce STR fragments; and determining the tandem repeat length of said fragments.

In some embodiments, forming the microfluidic droplets includes forming aqueous polymer gel droplets in a hydrophobic oil. In various embodiments, the method further includes isolating genomic DNA from the single cells in the polymer gel droplets.

In some embodiments, performing the amplification includes performing PCR in some embodiments, the length is determined by size-based separation. In some embodiments, determining the length includes performing capillary electrophoresis.

Another aspect involves a method for typing single-cell short tandem repeat DNA sequences by encapsulating a bead and a single cell in a droplet, such that a bead has one or more primers bound to it; performing a first PCR amplification within said droplet; and performing a second PCR amplification on an isolated bead, followed by determination of the tandem repeat lengths of the secondary products.

In some embodiments, the method further includes isolating genomic DNA from the single cell within the droplet. In some embodiments, isolating the genomic DNA includes immersing the encapsulated gel droplet in a cell lysis buffer to dissolve the cellular protein and membrane and releases the genomic DNA into the polymer gel. In some embodiments, determining the length includes a size-based separation. In some embodiments, determining the length includes performing capillary electrophoresis.

Another aspect involves a method of profiting single-cell short tandem repeat sequences by forming droplets including microbeads labeled with one or more primers and single cells; releasing the DNA from the single cell into each droplet; amplifying the DNA of each droplet such that the amplicons are bound to the bead; performing a second PCR amplification on isolated microbeads; and determining the size of the tandem repeat lengths of the secondary PCR products.

In various embodiments, releasing the DNA from the single cell into each droplet includes immersing the droplets in a cell lysis buffer. In some embodiments, determining the size includes performing capillary electrophoresis.

Another aspect involves a method for profiling single-cell short tandem repeat DNA sequences by forming oil in water emulsion droplets containing statistically dilute microbeads and single cells; releasing the DNA from the single cells into each droplet; performing a first PCR amplification of the emulsion droplets; and detecting single-cell STR profiles, such that the composition the droplets includes a liquid polymer capable of forming a gel.

Another aspect involves a method for profiling single-cell short tandem repeat DNA sequences by amplifying DNA of single cells encapsulated with microbeads in microfluidic droplets; and performing a secondary amplification on isolated microbeads, such that the microfluidic droplets include a material capable of allowing diffusion of enzymes and small reagents without allowing released cellular DNA to leave the droplet, and such that the microbeads are functionalized with primers. In some embodiments, the material is a liquid polymer capable of forming a gel.

Another aspect involves a method of typing short tandem repeat sequences by performing emulsion PCR amplification in single-cell microfluidic gel droplets, each droplet including at least one primer-coated microbead; and after isolating the microbeads, performing a secondary PCR amplification on the isolated microbeads to profile short tandem repeats.

Another aspect involves a system for forensic short tandem repeat (STR) identification of single-cell genomic DNA including a microfluidic droplet generator for generating gel droplets derived from an aqueous polymer gel, each droplet containing only one cell and one primer-functionalized bead; a PCR solution including forward and reverse primers, such that at least one forward or reverse primer is functionally identical to a forward or reverse primer on the primer functionalized bead; a centrifuge for isolating beads after emulsion oil PCR amplification of STR fragments; and a DNA analyzer for determining tandem repeat length of STR fragments after secondary PCR amplification.

In some embodiments, the aqueous polymer gel is an agarose gel. In various embodiments, the DNA analyzer includes a capillary electrophoresis system for determining STR length. In some embodiments, the microfluidic droplet generator generates the gel droplets in hydrophobic oil.

In various embodiments, the system also includes a cell lysis buffer, such that the cell lysis buffer dissolves cellular protein and membrane and releases genomic DNA into the polymer gel droplets. In some embodiments, the aqueous polymer gel allows diffusion of enzymes and small reagents but does not allow released genomic DNA to leave the gel droplets.

These and other aspects are described further below with reference to the drawings.

DETAILED DESCRIPTION

Figure 1:
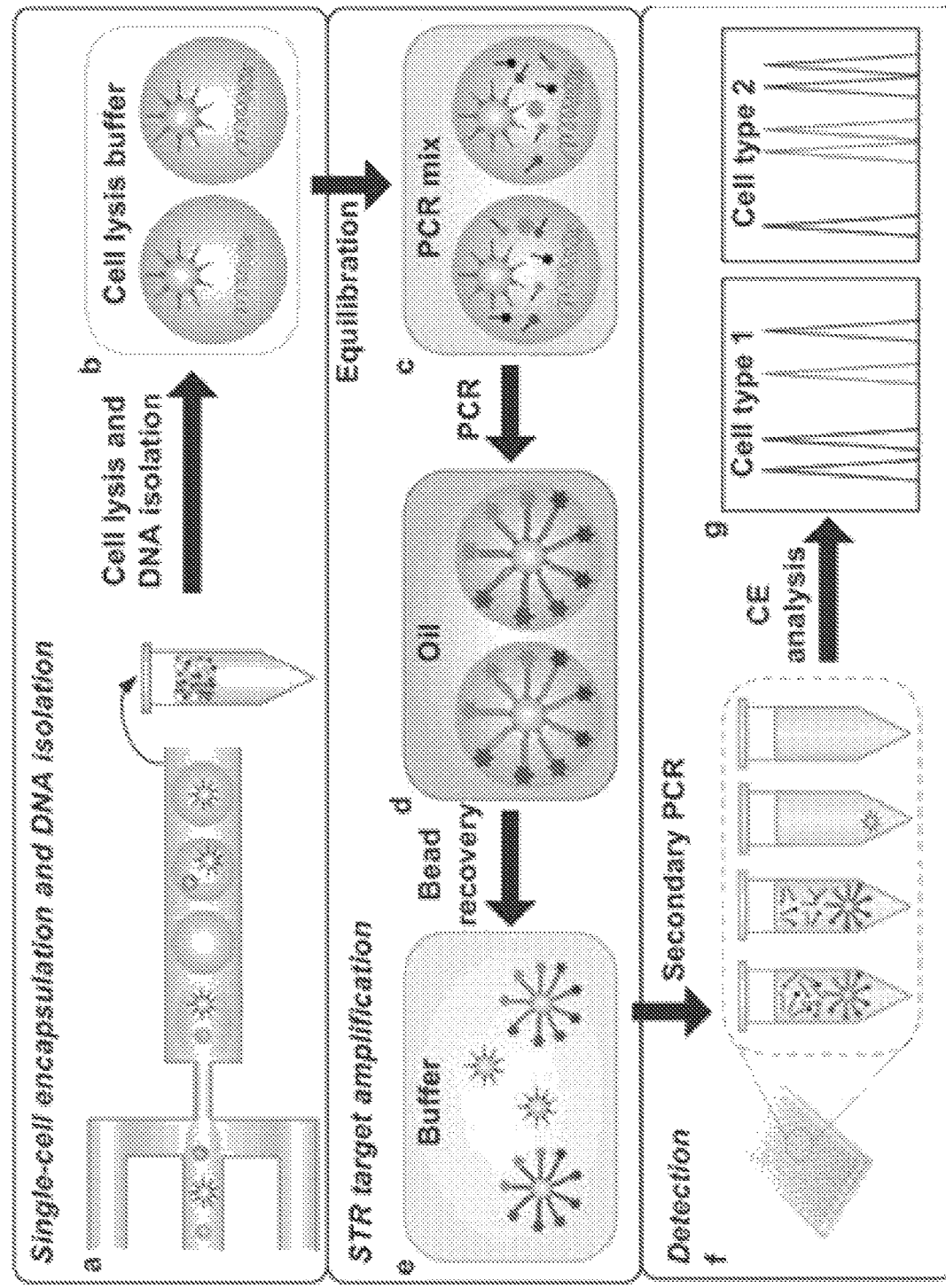
FIG. 1 shows an analytical procedure for single-cell forensic STR typing.

In the following description, numerous specific details are set forth to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

Aspects of the disclosure relate to methods of DNA profiling. In some implementations, the methods involve performing multiplex amplification of short tandem repeat DNA sequences from individual cells in microfluidic droplets and determining the tandem repeat length. In some implementations, the methods involve performing emulsion PCR amplification in single-cell microfluidic gel droplets, each droplet including a primer-coated microbead; and after isolating the microbeads, performing a secondary PCR amplification on the isolated microbeads. In some implementations, the methods involve amplifying DNA of single cells encapsulated with microbeads in a microfluidic droplet and performing a secondary amplification on isolated microbeads, such that the microfluidic droplets include a liquid polymer capable of forming a gel, and where the microbeads are functionalized with primers. In some implementations, the methods involve forming oil in water emulsion droplets containing statistically dilute microbeads and single cells; releasing the DNA from the single cells into each droplet; performing a first PCR amplification of the emulsion droplets; and detecting single-cell STR profiles. In some implementations, the methods involve forming droplets including microbeads labeled with one or more primers and single cells; releasing the DNA from the single cell into each droplet; amplifying the DNA of each droplet such that the amplicons are bound to the bead; performing a second PCR amplification on isolated microbeads; and determining the size of the tandem repeat lengths of the secondary PCR products. In some implementations, the methods involve forming microfluidic droplets containing statistically dilute microbeads and single cells; performing multiplex emulsion oil amplification of the short tandem repeat sequences in the microfluidic droplets to link the STR amplicons from single cells to the microbeads; isolating the individual microbeads and performing a secondary PCR amplification of the STR, sequences bound to each isolated bead to produce STR fragments; and determining the tandem repeat length of said fragments. In some implementations, the methods involve forming microfluidic droplets containing statistically dilute microbeads and single cells; performing multiplex emulsion oil amplification of the short tandem repeat sequences in the microfluidic droplets such as to bind the STR amplicons from single cells to individual microbeads; and isolating the individual microbeads and determining the tandem repeat length of the bead-bound amplicons. In some implementations, the methods involve forming aqueous polymer gel droplets in a hydrophobic oil such that a significant fraction of the gel droplets contain only one cell and only one primer-functionalized bead; isolating the gel droplets from the hydrophobic oil; immersing the encapsulated gel droplets in a cell lysis buffer, such that the cell lysis buffer dissolves the cellular protein and membrane and releases the genomic DNA into the polymer gel; washing the gel droplets to remove the cell lysis buffer; soaking the gel droplets in a PCR solution including forward and reverse primers, such that at least one forward or reverse primer is functionally identical to a forward or reverse primer on the primer-functionalized bead; performing emulsion oil PCR amplification of STR fragments, such that the emulsion oil PCR includes transferring replicas of desired STR targets from the single-cell genomic DNA onto the coencapsulated beads; isolating the beads; statistically diluting the isolated beads followed by performance of a secondary PCR amplification of the STR fragments; and determining the tandem repeat length of the STR fragments. In some implementations of the methods disclosed herein, droplets are formed from a liquid polymer capable of forming a gel, such as agarose. Further examples can include acrylamid, chitosan, gelatin, alginate, and pectin. Any material capable of allowing diffusion of enzymes and small reagents without allowing released cellular DNA to leave the droplet may be used. In some implementations, size-separation methods are used to determine size of PCR products. Examples include capillary electrophoresis. These and other aspects are discussed further below.

Short tandem repeat (STR) typing, the gold standard for human forensic identification, relies upon the collection of homogeneous, high-quality and concentrated. genetic samples from a crime scene. However, biological evidence samples often present mixtures of contributions (cells/cells or cells/DNA) from multiple individuals at relatively low concentrations. These complex biological samples generate mixed genotypes, presenting challenges in interpreting the results, especially when there are more than two contributors. Another difficulty arises when the perpetrator cells are much rarer than the victim cells, resulting in preferential amplification of the victim DNA. A variety of strategies have been developed to separate different cell populations prior to analysis to reduce the challenges in mixture interpretation, including differential extraction, filtration, fluorescence-activated cell sorting and microchip-based separation. More recently, laser capture microdissection and micromanipulation have been employed to analyze samples at the single-cell level. However, these methods are limited due to their complexity, low efficiency, low throughput, high risk of sample cross-contamination and/or lack of universality.

State-of-the-art microfluidic technology offers a promising strategy for the rapid generation of monodisperse microdroplets that can be used as miniaturized reactors for high-sensitivity single-cell analysis. Single cells are compartmentalized within the discrete aqueous droplets surrounded by an immiscible carrier oil, which dramatically reduces the possibility of cross-contamination among different cells. Due to the controllable droplet size and uniformity, the droplet content (e.g. the reagent composition and concentration) can also be precisely tuned to provide the desired microenvironment for individual cell reactions. The ultralow volume (femtoliter to nanoliter) of the droplets means that the nucleic acids and other biomolecules from a single cell are highly concentrated and detectable. Furthermore, the droplet technology allows massively parallel handling of millions of independent reactions with high throughput, thereby enabling the analysis of vast populations of single cells to detect rare events or to probe cellular heterogeneity.

Building upon traditional emulsion PCR technology with polydisperse droplets, we previously developed an efficient single-cell/molecule PCR method using uniform microfluidic nanoliter droplets, and used it to digitally detect pathogenic bacteria, cancer cells and molecular variation in heterogeneous populations with superior sensitivity and throughput. Robust mammalian cell lysis and DNA isolation in a highly parallel fashion was achieved by encapsulating single cells in agarose droplets. The agarose matrix conserved single-genome fidelity during various manipulations without inhibiting subsequent emulsion PCR assays. This mammalian cell genomic DNA isolation method is an enabling technology for STR amplification from single cells, especially in cases where only very small amounts of mixed evidence materials are available.

Here we present a single-cell STR typing method based on droplet microfluidics (FIG. 1). The technique enables the isolation of genomic DNA from a single cell and multiplex STR amplification within the same nanoliter agarose droplets. STR products are bound on the primer-functionalized microbeads coencapsulated in the droplets which are amplified by a secondary PCR reaction followed by capillary electrophoresis (CE) fragment size analysis. In some embodiments, the size of the droplets may be between about 100 pL to about 10 nL, or between about 1 nL and about 2 nL. Generally, emulsions in larger droplets may be unstable. In various embodiments, droplets too small in size undergo amplification less efficiently, and the cell and microbeads would not fit. In various embodiments, the diameters of the microbeads may be between about 2 microns and about 200 microns, or about 30 microns. As a proof-of-concept, we validated the technical performance of the method using a 9-plex STR system. The protocols for the microbead-based 9-plea PCR were first optimized both in bulk solution and in microdroplets using DNA standards. Individual cells from pure or mixed cell samples were then typed to evaluate the performance of single-STR analysis. In addition, the impact of cell-free DNA on single-cell typing was examined. Single-cell forensic STR amplification is a valuable new approach for analyzing dilute and mixed cellular populations.

Experimental

Microfluidic Droplet Generator Fabrication. The microfluidic droplet generator was fabricated using standard soft lithography. Briefly, a master mold was made of photoresist SU-8 2075 (MicroChem, Newton, Mass.) on a 4-inch silicon wafer (Addison Engineering, San Jose, Calif.). A polydimethylsiloxane (PDMS) replica was produced by pouring degassed PDMS prepolymer mixture (Sylgard 184; Dow Corning, Midland, Mich.) with a mass ratio of 10:1 (base: curing agent) onto the master, followed by baking at 80° C. for 2 h. After the PDMS replica and a pre-cleaned glass slide were treated by oxygen plasma, the device was immediately assembled and cured at 80° C. for 5 min. To increase the surface hydrophobicity, the microchannels were treated with 0.1% (heptadecafluoro-1,1,2,2-tetrahydrodecyl)dimethylchlorosilane (Gelest, Morrisville, Pa.) in 100% ethanol for 10 min, followed by baking at 100° C. overnight.

Primer-functionalized Bead Preparation. All primers used in this study were designed based on the sequences and fluorescence dye labeling scheme used in Promega PowerPlex® 16 System and purchased from IDT (Coralville, IA) (Table I).

TABLE I

Primer information for multiplex PCR

| Primer | | Sequence and Dye Labeling | Emulsion PCR (µM) | Secondary PCR (µM) |
|---|---|---|---|---|
| Amelogenin | F | [TAMRA]-CCCTGGGCTCTGTAAAGAA (SEQ ID NO: 1) | 0.18 | 0.18 |
| | R | ATCAGAGCTTAAACTGGGAAGCTG (SEQ ID NO: 2) | 0.018 | 0.18 |
| vWA | F | GCCCTAGTGGATGATAAGAATAATCAGTATGTG (SEQ ID NO: 3) | 0.022 | 0.22 |
| | R | [TAMRA]-GGACAGATGATAAATACATAGGATGGATGG (SEQ ID NO: 4) | 0.22 | 0.22 |
| D8S1179 | F | [TAMRA]-ATTGCAACTTATATGTATTTTTGTATTTCATG (SEQ ID NO: 5) | 0.64 | 0.64 |
| | R | ACCAAATTGTGTTCATGAGTATAGTTTC (SEQ ID NO: 6) | 0.064 | 0.64 |
| TH01 | F | [FAM]-GTGATTCCCATTGGCCTGTTC (SEQ ID NO: 7) | 0.21 | 0.21 |
| | R | ATTCCTGTGGGCTGAAAAGCTC (SEQ ID NO: 8) | 0.021 | 0.21 |

TABLE I-continued

Primer information for multiplex PCR

| Primer | | Sequence and Dye Labeling | Emulsion PCR (µM) | Secondary PCR (µM) |
|---|---|---|---|---|
| D3S1358 | F | ACTGCAGTCCAATCTGGGT (SEQ ID NO: 9) | 0.018 | 0.18 |
| | R | [FAM]-ATGAAATCAACAGAGGCTTGC (SEQ ID NO: 10) | 0.18 | 0.18 |
| D21S11 | F | ATATGTGAGTCAATTCCCCAAG (SEQ ID NO: 11) | 0.056 | 0.56 |
| | R | [FAM]-TGTATTAGTCAATGTTCTCCAGAGAC (SEQ ID NO: 12) | 0.56 | 0.56 |
| D5S818 | F | GGTGATTTTCCTCTTTGGTATCC (SEQ ID NO: 13) | 0.02 | 0.2 |
| | R | [JOE]-AGCCACAGTTTACAACATTTGTATCT (SEQ ID NO: 14) | 0.2 | 0.2 |
| D7S820 | F | [JOE]-ATGTTGGTCAGGCTGACTATG (SEQ ID NO: 15) | 0.45 | 0.45 |
| | R | GATTCCACATTTATCCTCATTGAC (SEQ ID NO: 16) | 0.045 | 0.45 |
| D13S317 | F | [JOE]-ATTACAGAAGTCTGGGATGTGGAGGA (SEQ ID NO: 17) | 0.1 | 0.1 |
| | R | GGCAGCCCAAAAAGACAGA (SEQ ID NO: 18) | 0.01 | 0.1 |

Abbreviations: F: Forward; R: Reverse.

The equimolar concentrations of 5'-amine modified primers with C12 spacers were conjugated on N-hydroxysuccinimide (NHS)-activated Sepharose beads (34 µm mean diameter; Amersham Biosciences, Piscataway, N.J.) via amine-NHS chemistry. The primers conjugated on beads included the reverse primers for Amelogenin, TH01, D13S317, D21S11, and D8S1179 as well as the forward primers for D3S1358, D5S818, vWA, and D7S820. The beads were stored in nuclease-free water at a concentration of 6×10$^6$ beads/mL at 4° C. until use.

Cell and DNA Sample Preparation. GM09947 (female) and GM09948 (male) human lymphoid cell lines (Coriell Institute for Medical Research, Camden, N.J.) were grown in RPMI 1640 medium (Life Technologies, Grand Island, N.Y.) supplemented with 10% fetal bovine serum (Life Technologies), 2 mM L-glutamine and 100 U/ml mg/mL streptomycin at 37° C. in a humidified incubator containing 5% CO$_2$. Once harvested, the cells were washed for 3 times in Dulbecco's PBS (DPBS; Life Technologies) and incubated at 37° C. prior to use. Samples were prepared by combining pre-warmed cell suspension (or DNA solution) and bead suspension with molten 3% (w/v) agarose solution using appropriate volumes to achieve desired concentrations. The stock agarose solution (3%) was prepared by dissolving ultra-low-gelling temperature agarose (Type IX; Sigma-Aldrich, St. Louis, Mo.) in DPBS at 70° C. for 5 h to remove bubbles and store at room temperature. For experiments involving GM9947A female and GM9948 male standard genomic DNA (Promega, Madison, Wis.), the DNA samples were diluted to desired concentrations using nuclease-free water. DNA concentration was calculated assuming 3 pg genomic DNA per copy.

Cell Encapsulation and Lysis. Cell/bead-encapsulated microdroplets were generated by infusing the aqueous samples and fluorinated oil (Bio-Rad, Hercules, Calif.) into the microfluidic droplet generator within a heated air stream (42-45° C.). The flow rates for the samples and oil were independently controlled by two syringe pumps (PIM 2000 infusion pump; Harvard Apparatus, Holliston, Mass.). The agarose droplets were collected in 0.5 mL PCR tubes and immediately cooled to 4° C. After agarose gelation for at least 1 h, the droplets were isolated from the oil using a cell strainer with 40 µm nylon mesh (RD Biosciences, San Jose, Calif.), followed by extensively washed with water. Cells in the droplets were lysed by combining equal volume of droplet suspension and 2× cell lysis buffer [1% SDS (Sigma-Aldrich), 200 mM EDTA, 20 mM Tris-HCl and 0.2 mg/mL proteinase K (Roche Applied Science, Indianapolis, Ind.)] and incubating at 37° C. overnight. Afterwards, the droplets were sequentially washed with 2% (w/v) Tween 20 (Sigma-Aldrich) in water once, 100% ethanol once and DPBS containing 0.02% (w/v) Tween 20 for 5 times. Tween 20 was used to prevent the attachment of droplets on the tube wall. The gelled droplets were finally washed with water once and resuspended in water.

Droplet PCR and Bead Recovery. Droplet PCR mix was prepared by mixing 1× AmpliTaq® Gold PCR buffer (Life Technologies), 1.5 mM MgCl$_2$ (Life Technologies), 200 µM dNTP (Qiagen, Valencia, Calif.), 4 µg/µL heat-inactivated BSA (Sigma-Aldrich), 0.01% Tween 80 (Sigma-Aldrich), 0.2 U/µL AmpliTaq® Gold DNA polymerase (Life Technologies), primer mixture and 3.6 µL agarose droplets encaging single-cell genomes in each 10 µL PCR reaction. The fluorescently labeled primers were ten times as many as their corresponding reverse-direction primers in the primer mixture (Table 1, as shown above). The mixtures were incubated in 0.5 mL PCR tubes for 40 min at 4° C. with occasional agitation to improve the transport of PCR components into agarose matrix structure. Fresh PCR carrier oil was prepared before each run of droplet PCR, containing DC 5225C formulation aid (Dow Chemical, Midland, Mich.), KF-7312J fluid (Shin-Etsu Silicones, Akron, Ohio), AR20 silicone oil (Sigma-Aldrich) and Triton X-100 surfactant (Sigma-Aldrich) with a mass ratio of 40:30:30:1. To redisperse the droplets, 150 µL carrier oil was added and mechanically vibrated at a frequency of 13 Hz for 30 s using a TissueLyser mixer (Qiagen). Each tube contained 10 µL PCR mix (including droplets) and 150 µL carrier oil to ensure uniform heating when fitting into the thermoblock of PTC100 thermocycler (MJ Research, Waltham, Mass.). The thermal cycling condition was composed of initial activation of the AmpliTaq®, Gold DNA polymerase at 95° C. for 10 min, followed by 10 cycles of 94° C. for 1 min, 58° C. for 1 min, 70° C. for 1.5 min, 22 cycles of 90° C. for 1 min, 58° C. for 1 min, 70° C. for 1.5 min, and a final extension step for 30 min at 60° C. The samples were then cooled to 4° C. to enable agarose gelation.

Following STR amplification, the gelled droplets were harvested by centrifuging at 250 g for 1 min, and sequentially washed with 100% isopropanol once, 100% ethanol once and DPBS containing 0.02% Tween 20 for 5 times to remove the residual oil. The beads carrying STR products were released from the droplets by melting the agarose at 60° C. for 15 min. The beads were washed with 0.1% SDS once to remove BSA and DPBS for 8 times to remove the DNA fragments unlinked to the beads. Finally, the beads were resuspended in water and stored at 4° C.

STR Product Detection. Secondary PCR was performed on the STR-conjugated beads to transfer the STR information into free solution for detection. The DNA-carrying beads were diluted at appropriate concentrations (0.2-20 beads/reaction) in standard 96-well PCR plates or PCR tubes to serve as the DNA templates fur reamplification. The secondary PCR was conducted in 12.5 µL reactions using PCR mix containing 1× Gold ST*R buffer (Promega), 0.1 U/µL AmpliTaq® Gold DNA polymerase, primer mixture, nuclease-free water and bead solution. The fluorescently labeled primers had the same amounts as their corresponding reverse-direction primers in the primer mixture (Table I, as shown above). The PCR protocol involved 10 min hot start at 95° C., then 10 cycles of 94° C. for 30 s, ramp at the rate of 0.5° C./s to 58° C., hold for 30 s, ramp at the rate of 0.3° C./s to 70° C., hold for 45 s, followed by 15 cycles of 90° C. for 30 s, ramp at the rate of 0.5° C./s to 58° C. hold for 30 s, ramp at the rate of 0.3° C./s to 70° C., hold for 45 s, and a final extension step at 60° C. for 30 min. The amplified products in five solutions were processed for fragment size analysis on Applied Biosystems 3730XL DNA Analyzer using Hi-Di formamide (Life Technologies) and GeneScan 500 ROX size standard (Life Technologies). The data were analyzed using Peak Scanner software (Life Technologies).

Results and Discussion

We have developed a highly sensitive and selective microfluidic-droplet-based approach fur high-throughput single-cell forensic STR typing. The overall process is illustrated in FIG. 1. In (a), statistically dilute individual cells are together with primer-functionalized microbeads encapsulated within agarose microdroplets using a microfluidic droplet generator, (b) shows that the gelled droplets are incubated in cell lysis buffer to release genomic DNA into the get matrix. In (c), the PCR components are diffused into the gel droplets by equilibrating in PCR mix. In (d), after the droplets are redispersed in oil, emulsion PCR is performed with a thermal cycler. In (e) after the first STR amplification, beads are recovered by melting the agarose. In (f), statistically dilute secondary PCR is conducted starting from single beads in standard PCR plates. In (g) the STR products from the positive single bead amplifications are processed using conventional CE system for fragment size analysis. Different types of intact cells in a cellular mixture yield distinct single-cell STR profiles. The total analysis is accomplished in about 22 h, including 3.5 h working time and 18.5 h waiting time for cell lysis (10 h), droplet PCR (3.5 h), secondary PCR (3 h) and CE analysis (2 h). Single cells are initially compartmentalized and lysed to liberate genomic DNA within nanoliter agarose droplets. Massively parallel droplet PCR is then implemented to amplify the STR targets from individual cells and to transfer the STR information onto the coencapsulated primer-functionalized beads. Finally, the STR products bound on individual beads are transferred to free solutions by performing a statistically dilute secondary PCR in standard plates or tubes, followed by conventional CE fragment size analysis.

Figure 2A:
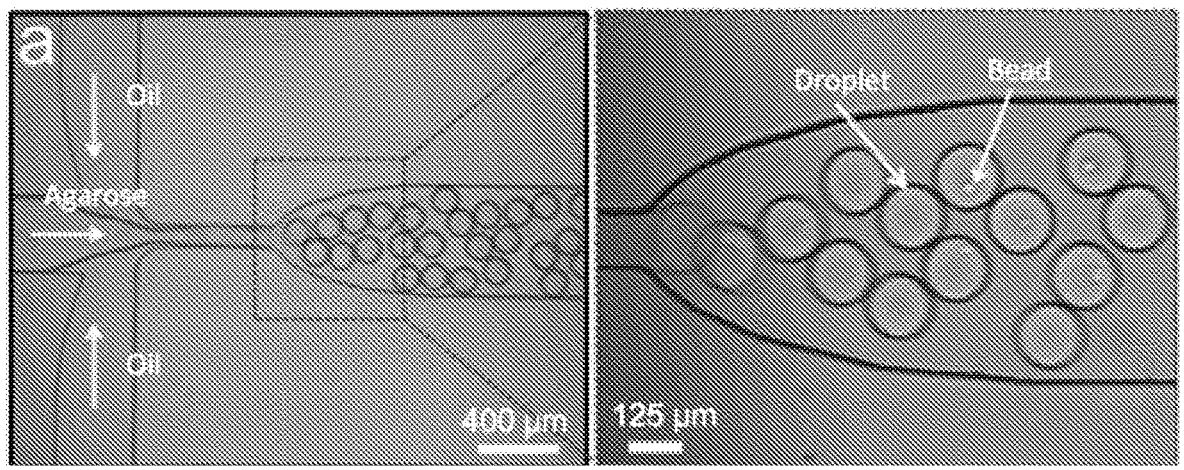
FIGS. 2A-2C depict images of agarose microdroplet generation and manipulation.
Figure 2B:
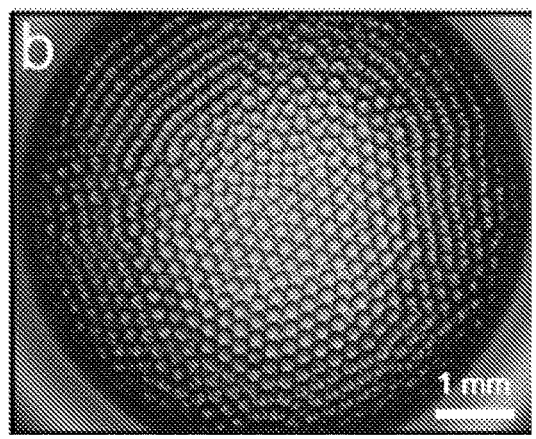

The PDMS/glass microfluidic droplet generator was constructed to produce monodisperse agarose microdroplets based on a flow-focusing channel geometry. The dispersed (aqueous) phase containing primer-functionalized microbeads, cells/DNA and 3% agarose flowed in the central channel while the continuous (oil) phase flowed in the two side channels, as shown in FIG. 2A. Microdroplet generation is based on a flow-focusing structure fabricated in a PDMS/glass microfluidic device. Primer-functionalized beads and the desired number of cells (or genomic DNA when desired) are encapsulated within the droplets. Fluorinated oil and 3% agarose solution are infused into the channel using a syringe pump. With optimized channel dimensions (125 µm wide nozzle, 130 µm deep) and flow rates (40 µL/min for aqueous phase and 100 µL/min for oil phase), 1.5 nL agarose droplets could be generated with a high frequency of ~444 Hz in the fluorinated oil. Single cells (or genomic DNA when desired) along with microbeads were stochastically encapsulated into the droplets following Poisson statistics.

Ultra-low-gelling temperature agarose with a gel point about 8-17° C. and a remelting point of ≤50° C. was selected to avoid agarose gelation during droplet generation and to provide a convenient medium for template DNA capture and manipulation. The most significant advantage of agarose droplets is their ability to rapidly transform into microgels by simply cooling to below the gelling temperature. FIG. 2A shows the highly uniform gel droplets suspended within fluorinated oil in a 96-well plate. The network structure of the gelled porous matrix enabled the diffusion of reagents (i.e. lytic reagents and PCR components) into interior, while encaging the high-molecular-weight DNA within the droplets. Other examples of polymer gels that may be used include acrylamid, chitosan, gelatin, alginate, and pectin.

Figure 2C:
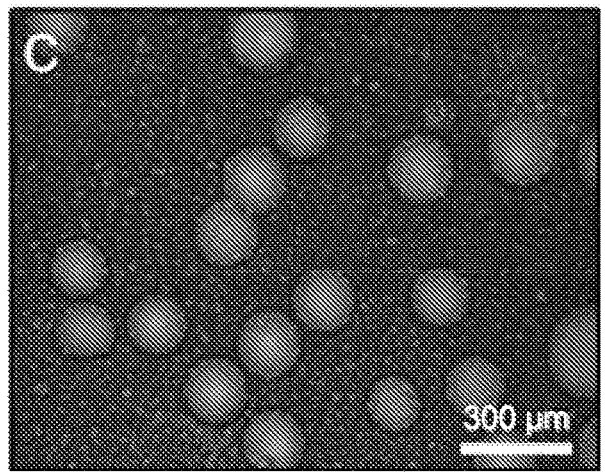

The incorporation of the cell lysis and DNA isolation step can be important for PCR-based STR analysis as the vast majority of human cellular genomic DNA is tightly packaged in the nucleus. Histones and other DNA-associated nuclear proteins are enzymatically digested to make the DNA more accessible and to remove potential PCR inhibitors. In addition, the microgel enables mechanical manipulation and long-term storage of millions of microdroplets simultaneously while preserving single-genome fidelity. The mechanical properties of the gel microdroplets were adjusted by the concentration of agarose in the feed solutions. We found that 1.5% (w/v) of agarose gel provided sufficient strength without hindering molecular diffusion and compromising PCR performance. During PCR thermal cycling, the agarose was molten and stayed in the liquid state during the whole process. This feature improved the mixing of PCR components and DNA products within the nanoliter reactors. The droplets remained intact after PCR, though a slightly deformation was observed, as demonstrated in FIG. 2C. Intact droplets after 32 cycles of emulsion PCR in freshly prepared silicon oil mixture.

Figure 2D:
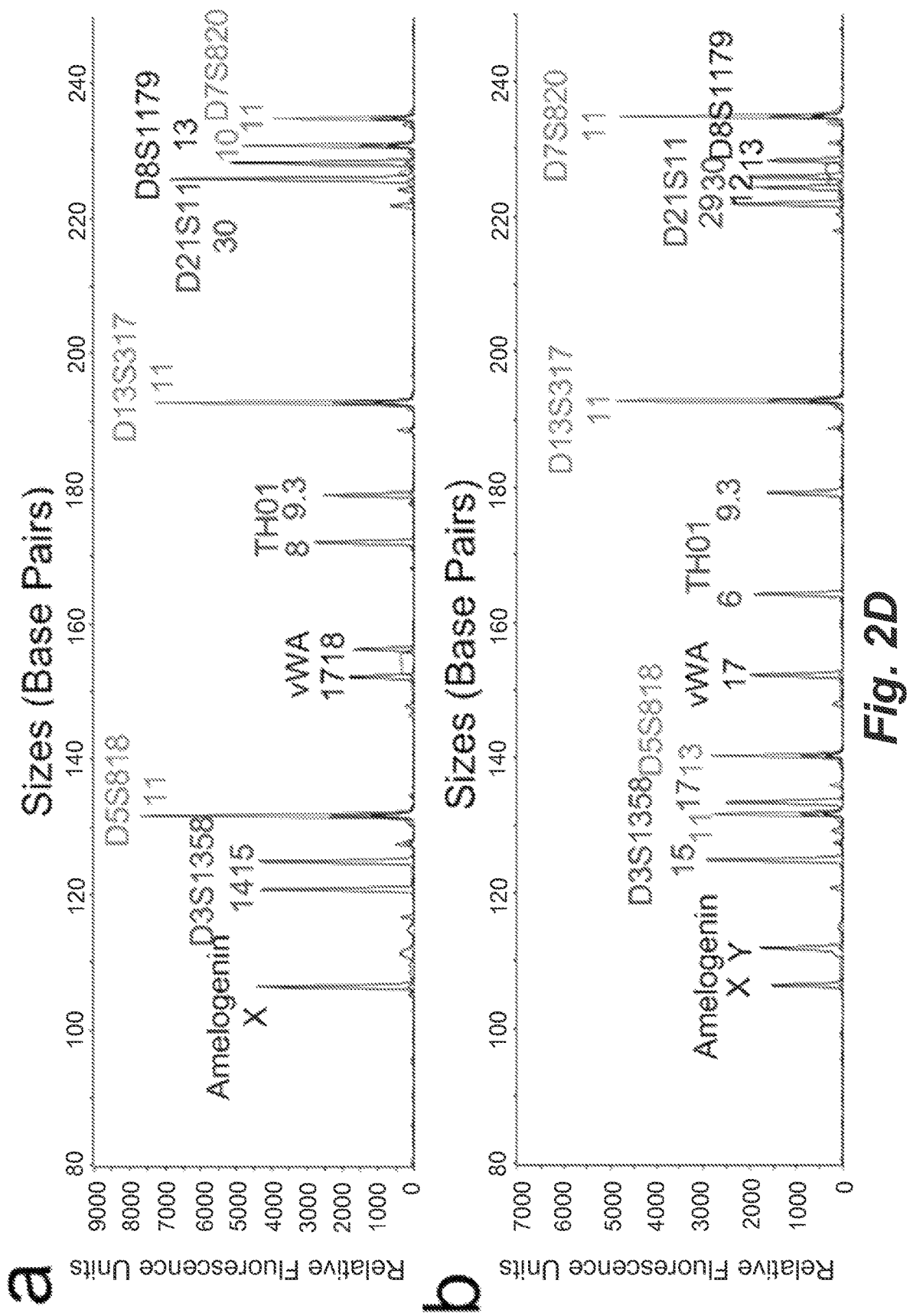
FIG. 2D shows representative 9-plex STR profiles resulting from PCR amplification of (a) 9947A female genomic DNA and (b) 9948 male genomic DNA at high concentrations in bulk solutions containing multiplex-further-functionatized microbeads.
Figure 2E:
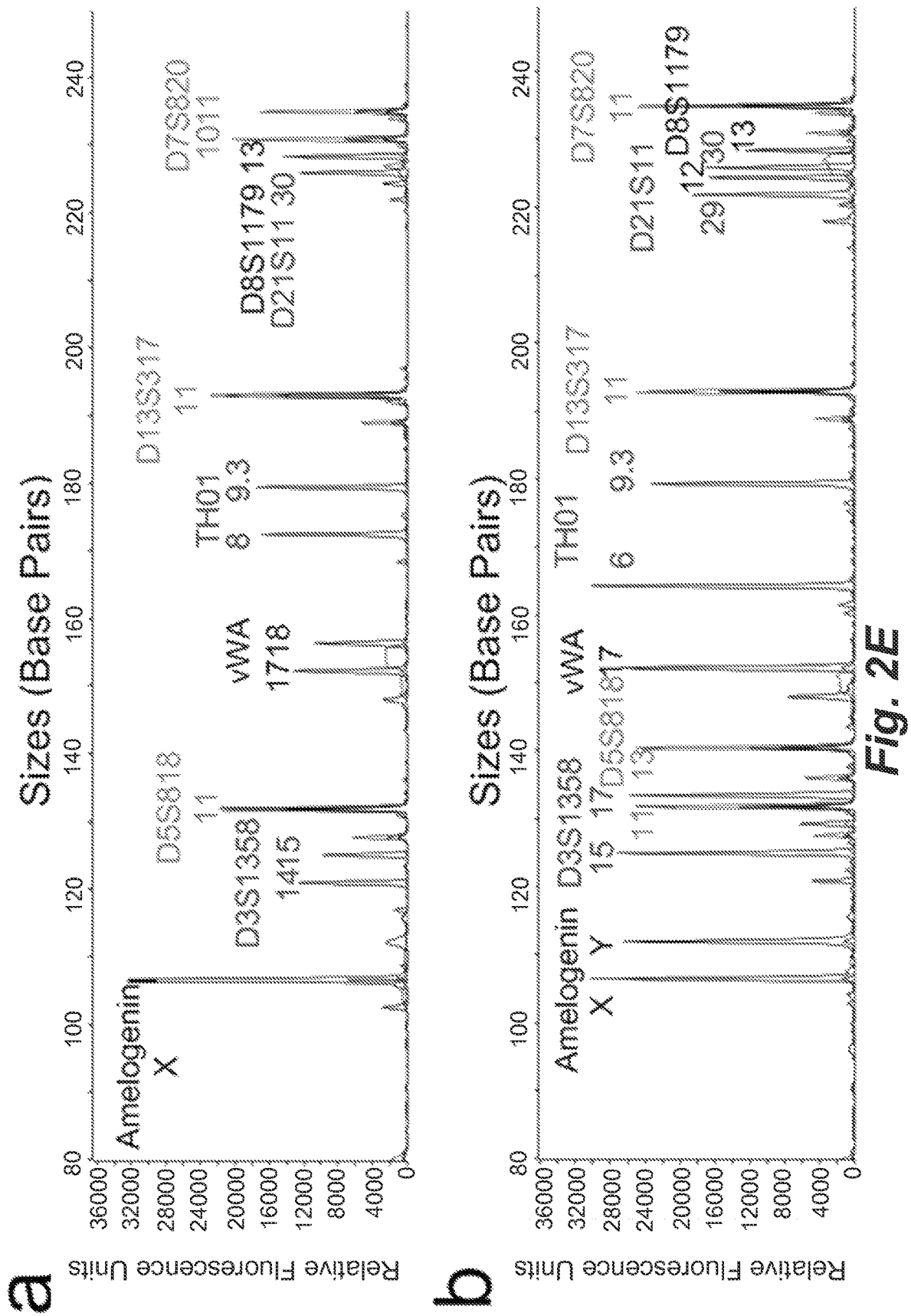
FIG. 2E shows representative 9-plex STR profiles resulting from secondary PCR amplification of single beads carrying STR products of (a) 9947A female genomic DNA and (b) 9948 male genomic DNA.

To explore the utilization of this method for forensic DNA typing, a 9-plex STR system was developed with eight core STR loci (i.e. D3S1358, D5S818, D7S820, D8S1179, D13S317, D21S11, vWA, and TH01) from the combined DNA index system (CODIS) and Amelogenin for sex-typing and sample quality evaluation. We first validated the microbead-based solid-phase PCR for 9-plex STR typing with standard 9947A female and 9948 male genomic -DNA in bulk solutions. The STR profiles of both types of DNA were in agreement with the established locus information (Table II (below)), and the peaks are balanced under the optimized PCR condition (FIG. 2D). The PCR was performed with 32 cycles from 40 pg/µL (~13 copies/µL) of the genomic DNA. The PCR products in free solution were processed by a conventional CE system for fragment sizing analysis. These traces illustrate the success in balancing the solid-phase 9-plex PCR involving microbeads. Previous work indicated that up to 100 attomoles of total amplicons were expected to be carried on an individual 34 µm diameter bead. The success of the secondary PCR verified that this amount of STR template was sufficient for high-quality forensic analysis by CE (FIG. 2E). The amplicon-bound beads were prepared by performing 32 cycles of PCR seeded with isolated DNA in bulk solution. The PCR starting from single beads was performed in standard PCR plates with 30 cycles. These traces illustrate the success in balancing the 9-plex PCR starting from a single-beads carrying STR products.

TABLE II

Locus-specific information for 9947A female and 9948 male genomic DNA

| STR Locus | 9947A female DNA | | 9948 male DNA | |
| --- | --- | --- | --- | --- |
| | Repeat number | Amplicon size (bp) | Repeat number | Amplicon size (bp) |
| Amelogenin | X, X | 106 | X, Y | 106, 112 |
| vWA | 17, 18 | 151, 155 | 17, 17 | 151 |
| D8S1179 | 13, 13 | 227 | 12, 13 | 223, 227 |
| TH01 | 8, 9.3 | 172, 179 | 6, 9.3 | 164, 179 |
| D3S1358 | 14, 15 | 123, 135 | 15, 17 | 127, 135 |
| D21S11 | 30, 30 | 227 | 29, 30 | 223, 227 |
| D5S818 | 11, 11 | 135 | 11, 13 | 135, 143 |
| D7S820 | 10, 11 | 231, 235 | 11, 11 | 235 |
| D13S317 | 11, 11 | 181 | 11, 11 | 181 |

Figure 3A:
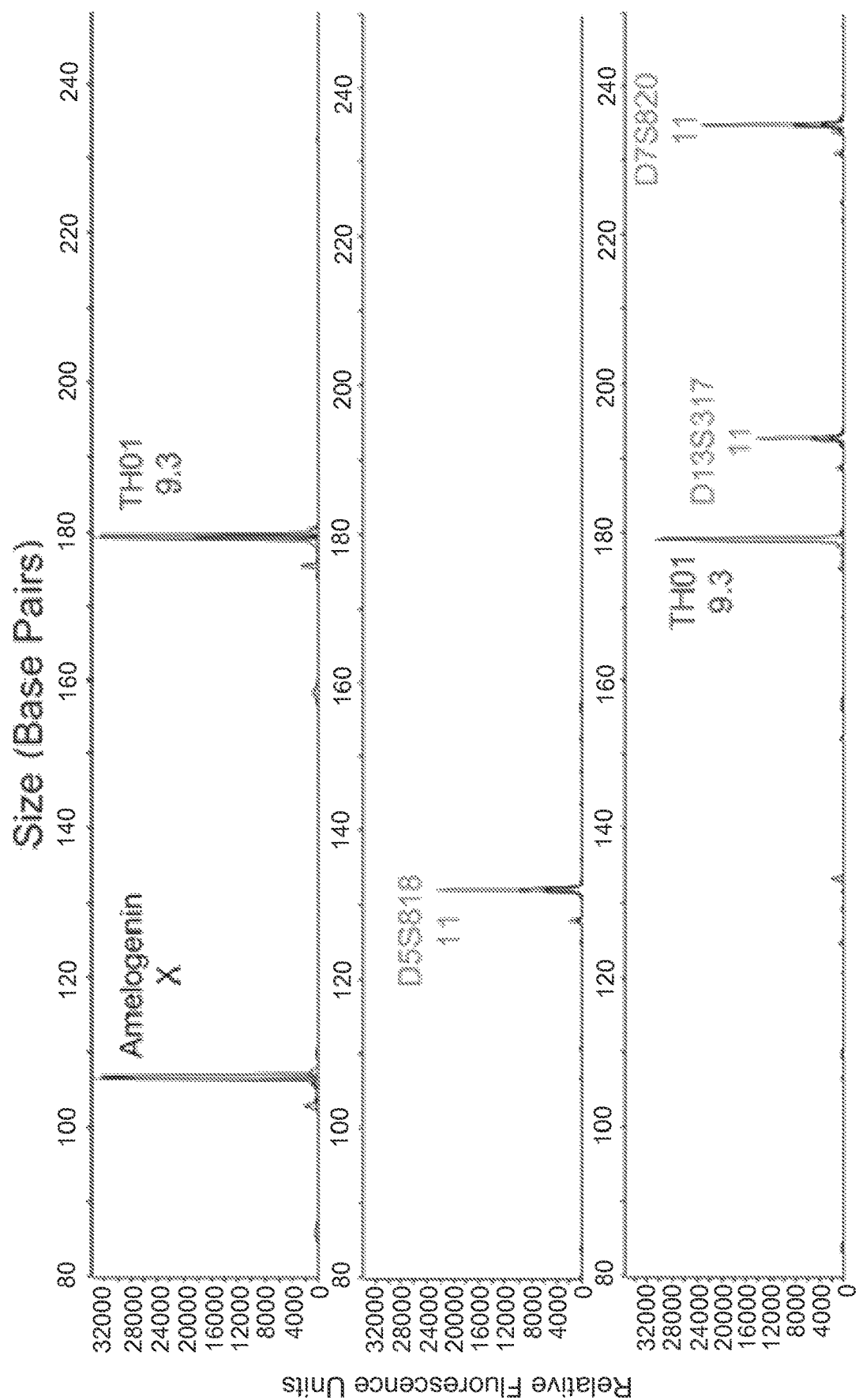
FIG. 3A shows representative STR profiles resulting from microdroplets containing on average 0.2 copies of 9947A female genomic DNA and 0.9 beads per droplet.

Single-molecule emulsion PCR was initially performed with 9947A female genomic DNA based on the optimized amplification protocols (FIG. 3A). A DNA concentration of 0.2 copies/droplet (corresponding to 1.8 alleles/droplet) was tested, while maintaining bead concentration at 0.9 beads/droplet on average. At this DNA concentration, it is predicted that 83% of the beads will have one or more STR templates and each individual unique heterozygous STR target will appear with a probability of 9.5%. In the secondary PCR, beads were diluted to 0.15 beads/reaction in order to reduce the probability of more than one bead appeared in each well of the PCR plate to 1% (13% of reactions involving only one bead). Note that because this is a true digital amplification, when a template is present there is only one copy leading to uniform peak heights. As expected, in FIG. 3A incomplete STR profiles were obtained and each DNA-carrying bead exhibited distinct STR genotypes, consistent with random genomic template fragment encapsulation within the microdroplets. The low DNA input of 0.2 copies/droplet resulted in only 1 to 3 peaks detected from an individual bead.

Figure 3B:
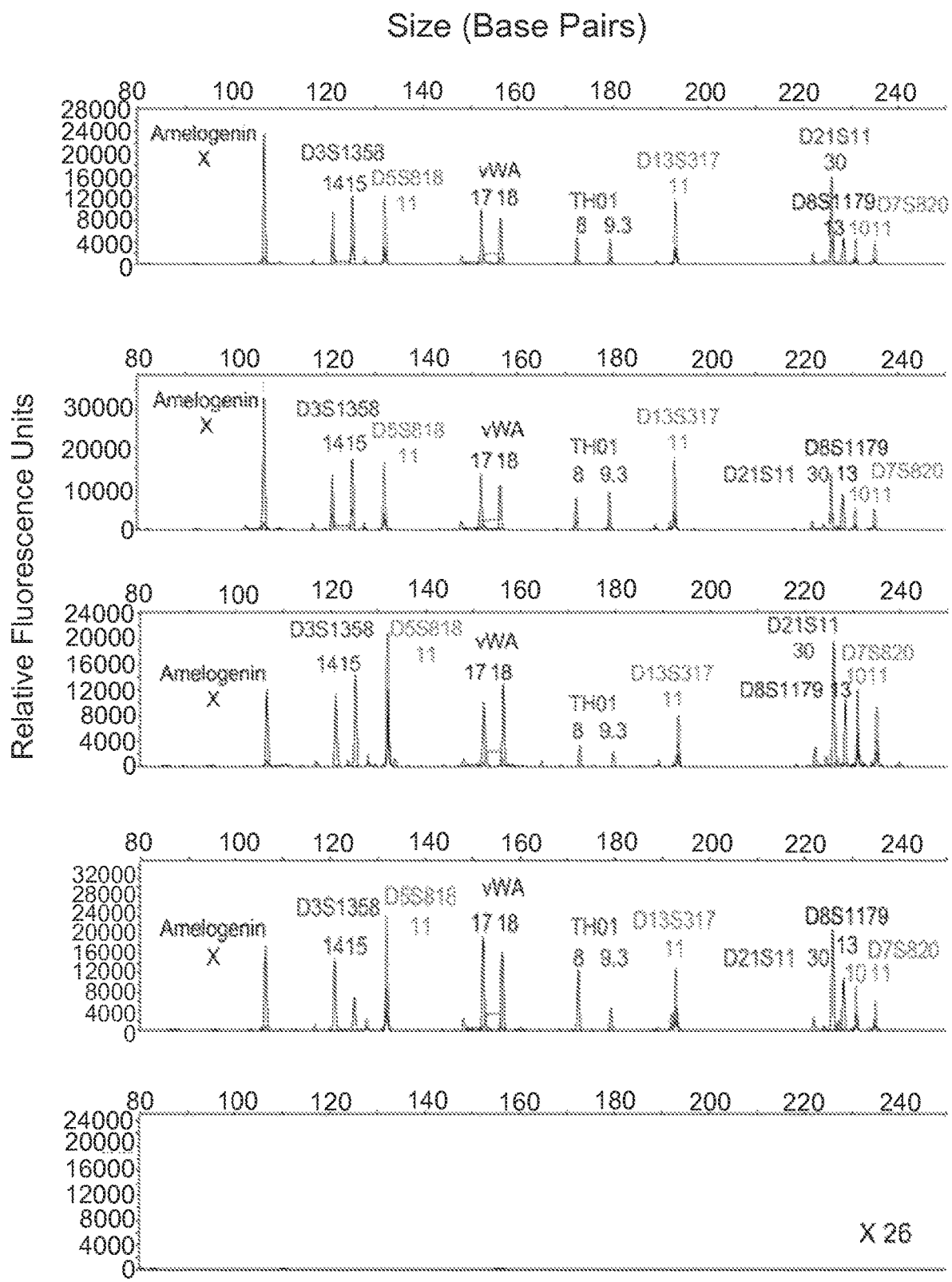
FIGS. 3B and 3C show single-cell STR profiles resulting from microdroplets containing on average 0.15 GM09947 human (female) (b) or GM09948 human (male) (c) lymphoid cells and 0.9 beads per droplet.
Figure 3C:
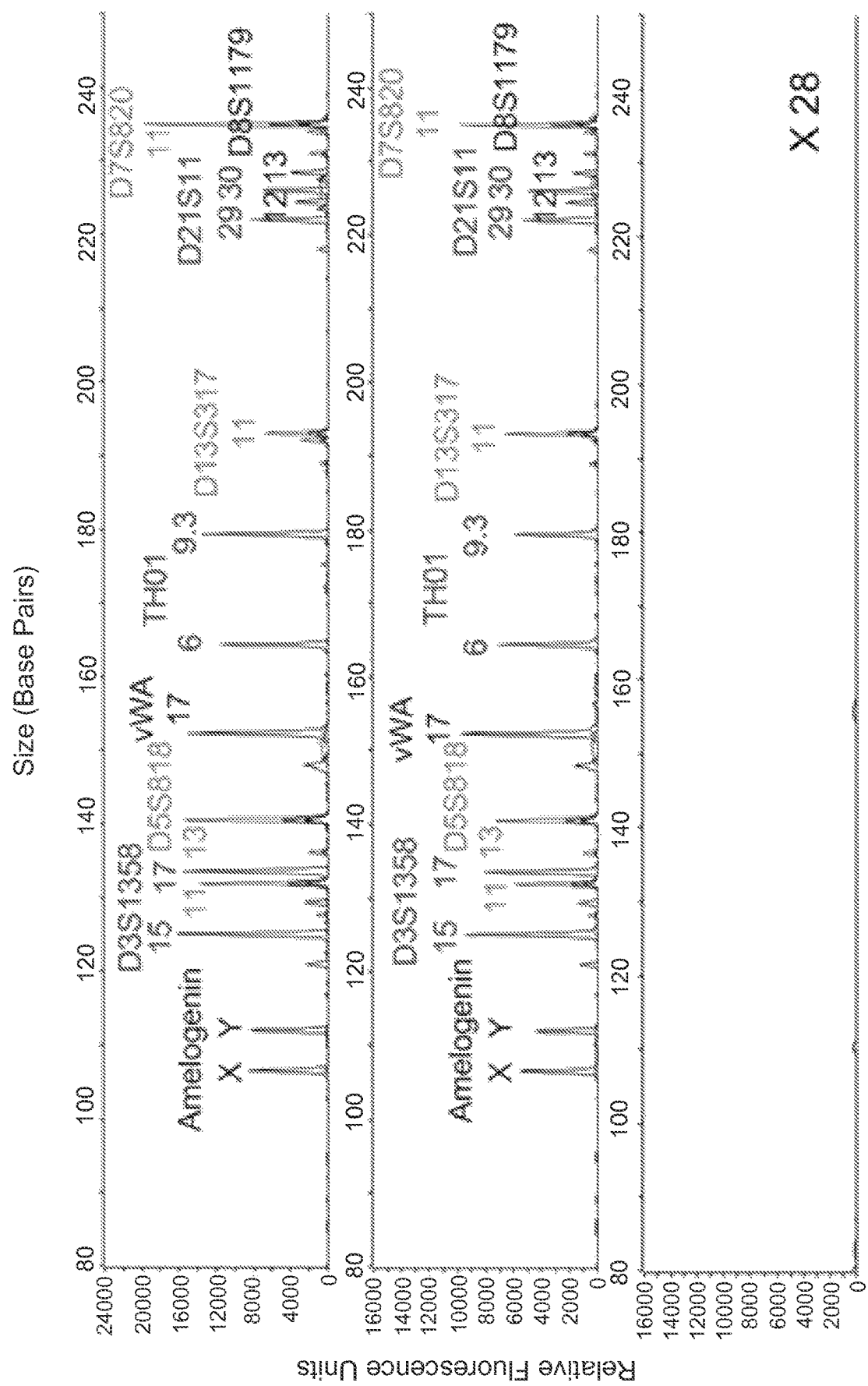

Single-cell STR typing was then demonstrated using pure cell populations of two standard cell lines: GM09947 (female) and GM09948 (male) human lymphoid cells. Each droplet contained on average 0.15 cells and 0.9 microbeads, predicting that 14% of the beads should be bound with STR amplicons (positive). The low cell frequency ensured that no more than one cell was encapsulated in a droplet. 30 samples were tested in the secondary PCR with a bead concentration of 0.9 beads/reaction which predicts 0.14×0.9=0.126 positive beads/reaction. The results in FIGS. 3B and 3C show that there were 4 and 2 positive analyses as well as 26 and 28 null results for GM09947 and GM09948 cells, respectively, in close agreement with the value of 12% predicted by the Poisson distribution. In contrast to the genomic DNA encapsulation in FIG. 3A, full STR profiles were obtained from single GM09947 cells (13 peaks) and single GM09948 cells (15 peaks) with relatively uniform peak intensities. All alleles were correctly called, and no allelic drop-in and drop-out was observed in both cell types. This is expected because when a cell is present the number of STR template copies in the droplet reactor is digitally defined by the genome. The stutter percentages for all allele peaks were below 15%, so the stutter products can be ignored as biological artifact of the samples. Furthermore, all the profiles of the negative samples were clean, confirming the absence of contamination. The 'all or nothing' feature of the single-cell droplet PCR event indicates the conservation of single-cell-genome integrity within the compartmentalized droplets during various manipulations and the successful transfer of STR information from single cells to individual microbeads.

Figure 4A:
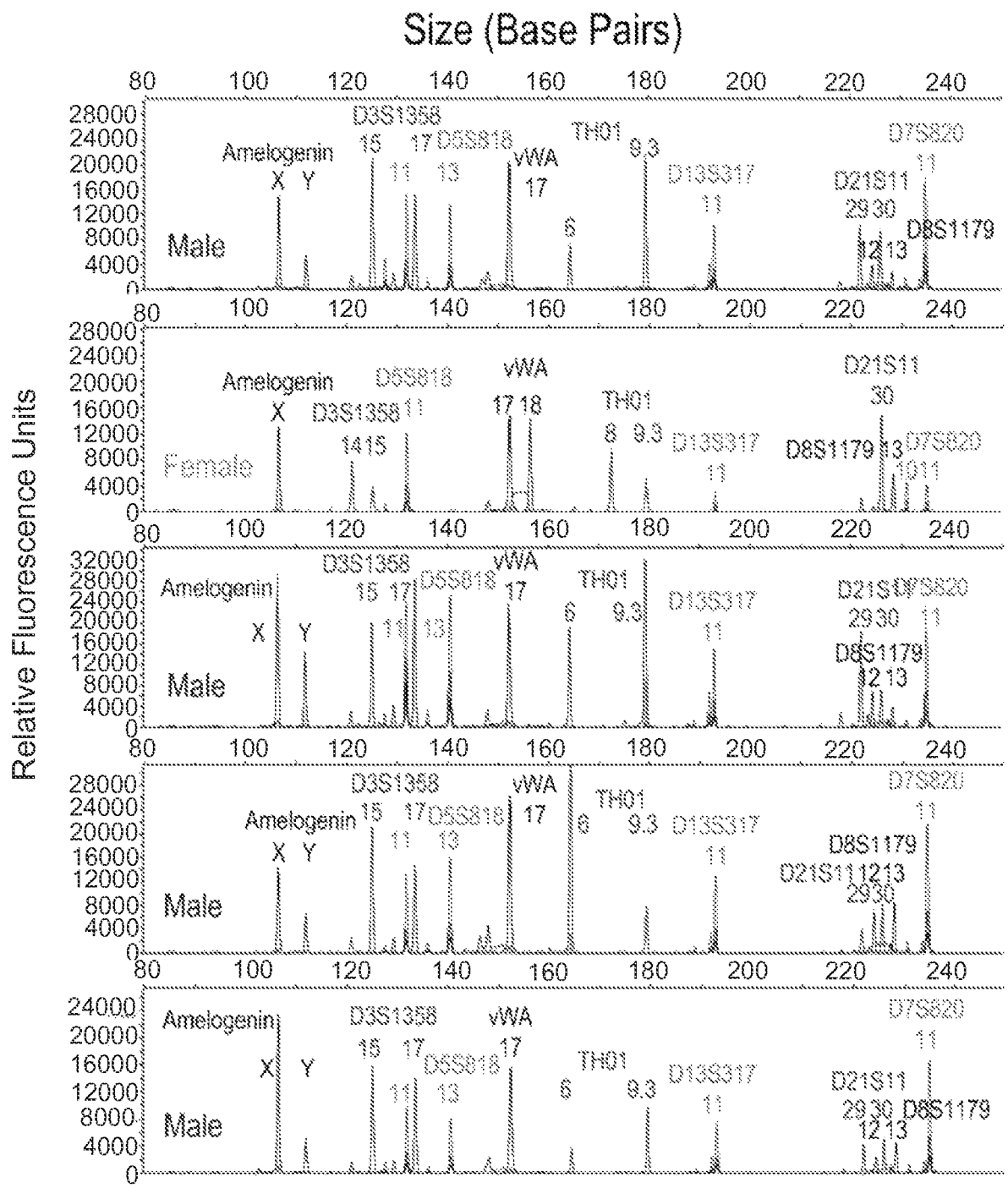
FIGS. 4A and 4B show single-cell STR profiles resulting from microdroplets containing a mixture of 0.005 GM09947 human (female) lymphoid cells and 0.005 GM09948 human (male) lymphoid cells per droplet together with 0.9 beads per droplet on average.
Figure 4B:
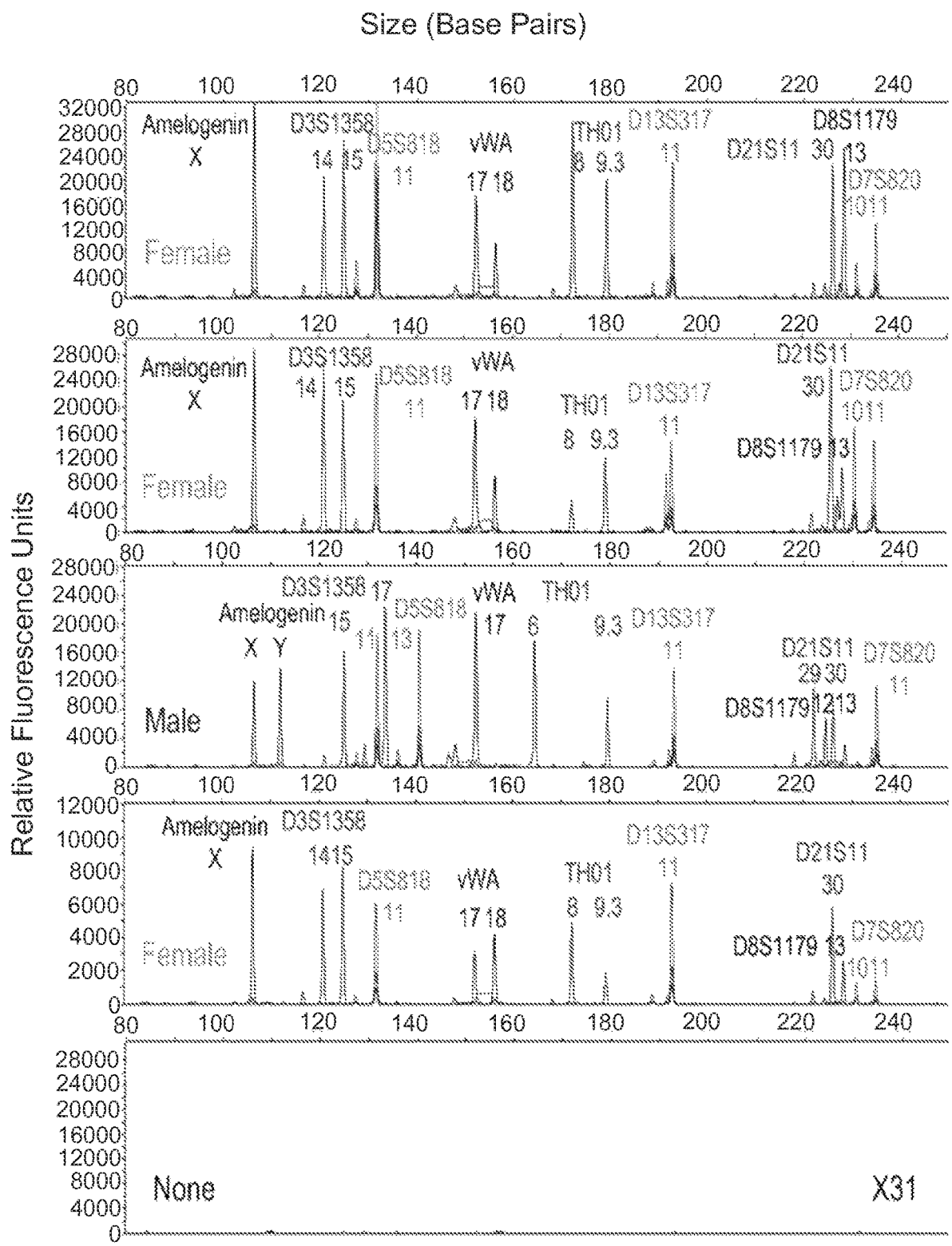
Figure 9:
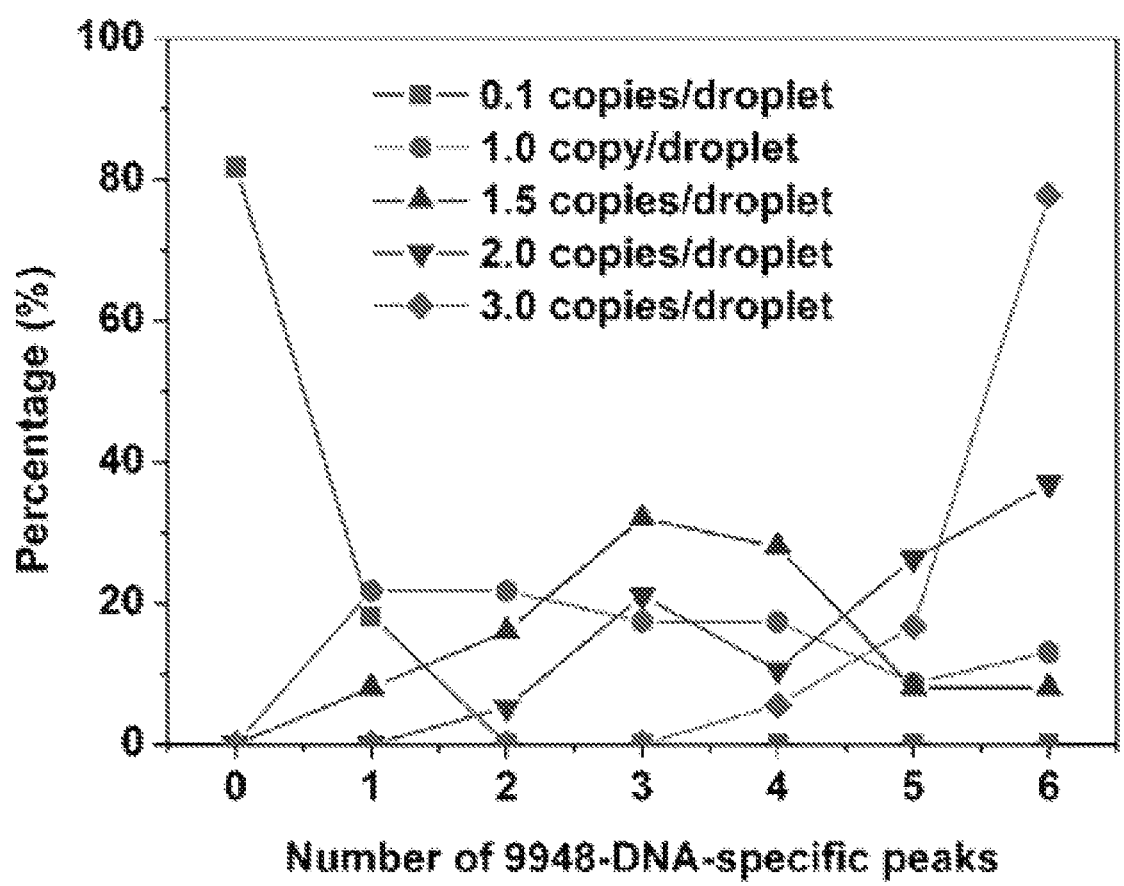
FIG. 9 shows a graph for percentage of STR profiles in single-cell STR typing in presence of cell-free contaminating DNA.

To access the selectivity and sensitivity of the single-cell STR typing method, we performed droplet PCR using mixtures of GM09947 (female) and GM09948 (male) human lymphoid cells at various female-to-male cell ratios (1:1, 2:1, 5:1 and 10:1). The total cells were diluted to 0.01 cells/droplet on average to eliminate the chance of cell clumping in the agarose solution, while the bead concentration remained unchanged (0.9 beads/droplet). Since only 1% of the beads should be positive, the number of the secondary PCR reactions was increased to 40-100, and the bead concentration in the secondary PCR step was increased to 20 beads/reaction resulting in 0.2 positive beads/reaction. In the experiment at the input cell ratio of 1:1 shown in FIGS. 4A and 4B, 9 positive samples were obtained in 40 reactions, which was consistent with the theoretical prediction of 18%. Under these statistically dilute conditions it is expected that approximately 1% of the beads will be conjugated with the STR products from either type of cell. In total 40 samples were tested in secondary PCR using 20 beads per reaction (predicting 2.0×0.01=0.2 positive beads per reaction). The high bead concentration was used to ensure that more positive beads could be analyzed with fewer secondary PCR reactions. There were 9 positive analyses (consistent with the theoretical value of 18% predicted by Poisson distribution), in which 4 STR profiles were from GM09947 cells and 5 were from GM09948 cells. 31 samples yielded null results in the secondary PCR, as exemplified in the bottom panel. In all cases, 30 cycles of emulsion PCR and 25 cycles of secondary PCR were performed. Among the 9 positive samples, we detected the complete STR profiles from 4 single GM09947 cells and 5 single GM09948 cells. No mixed STR profiles were detected. The quality of the STR profiles was similar to that obtained using pure cell population in terms of the stutter formation (below 15%) as well as incidence of allelic drop-in and drop-out. Nevertheless, the heterozygous peaks for some STR loci such as Amelogenin and TH01 were not fully balanced. This observation is possibly due to the stochastic effects when amplifying low levels of target DNA molecules.

Figure 4C:
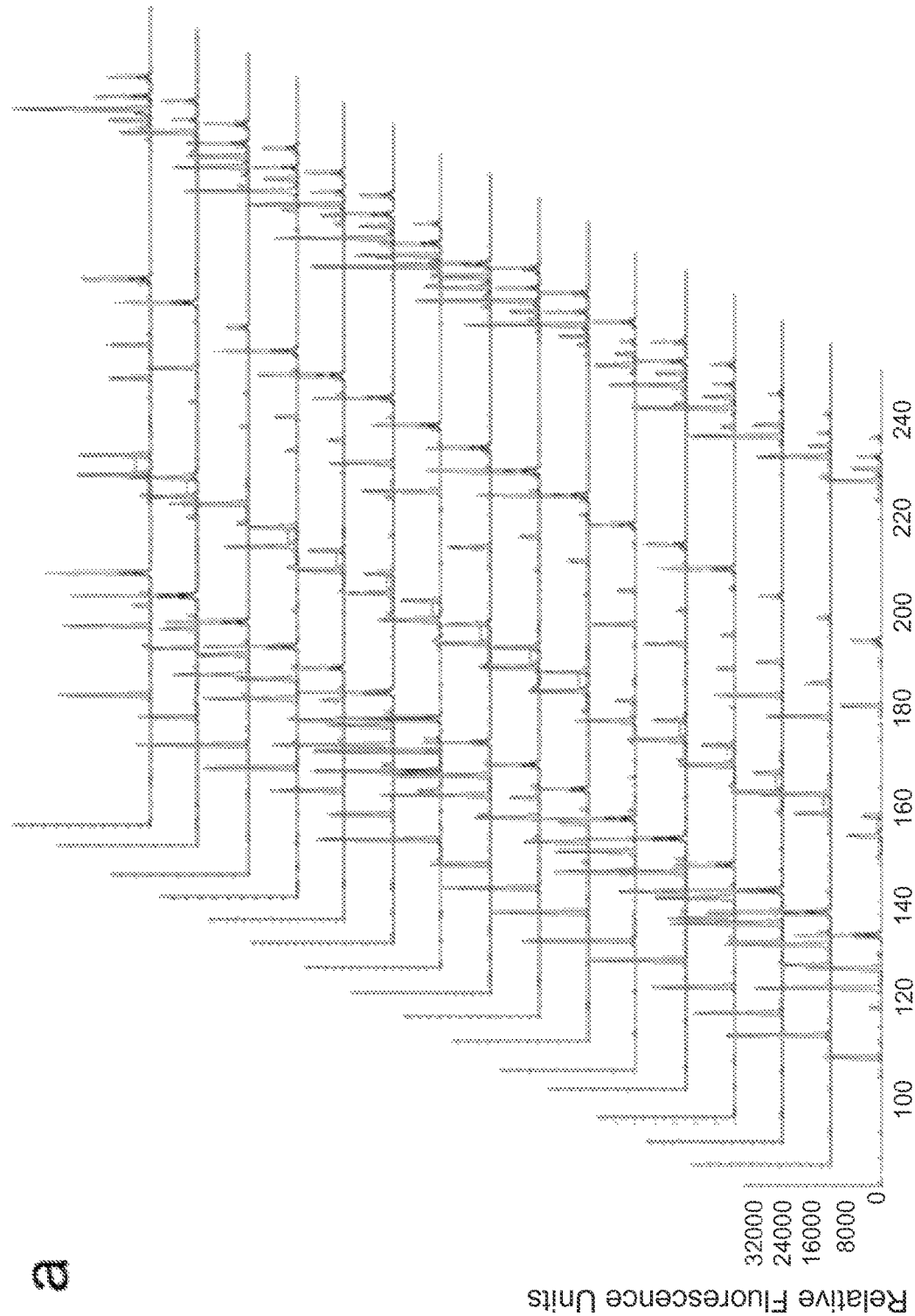
FIGS. 4C and 4D show single-cell STR profiles resulting from microdroplets containing on average 0.01 GM09947 human (female) and GM09948 human (male) lymphoid cells with a ratio of 5:1 as well as 0.9 beads per droplet.
Figure 4D:
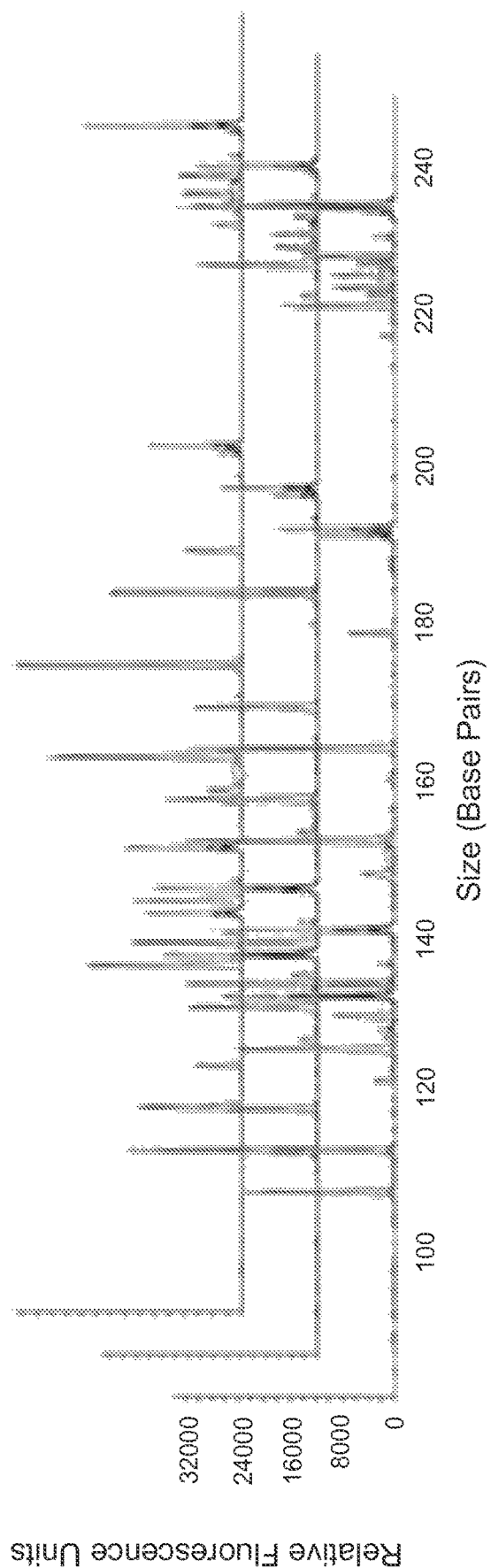
Figure 4E:
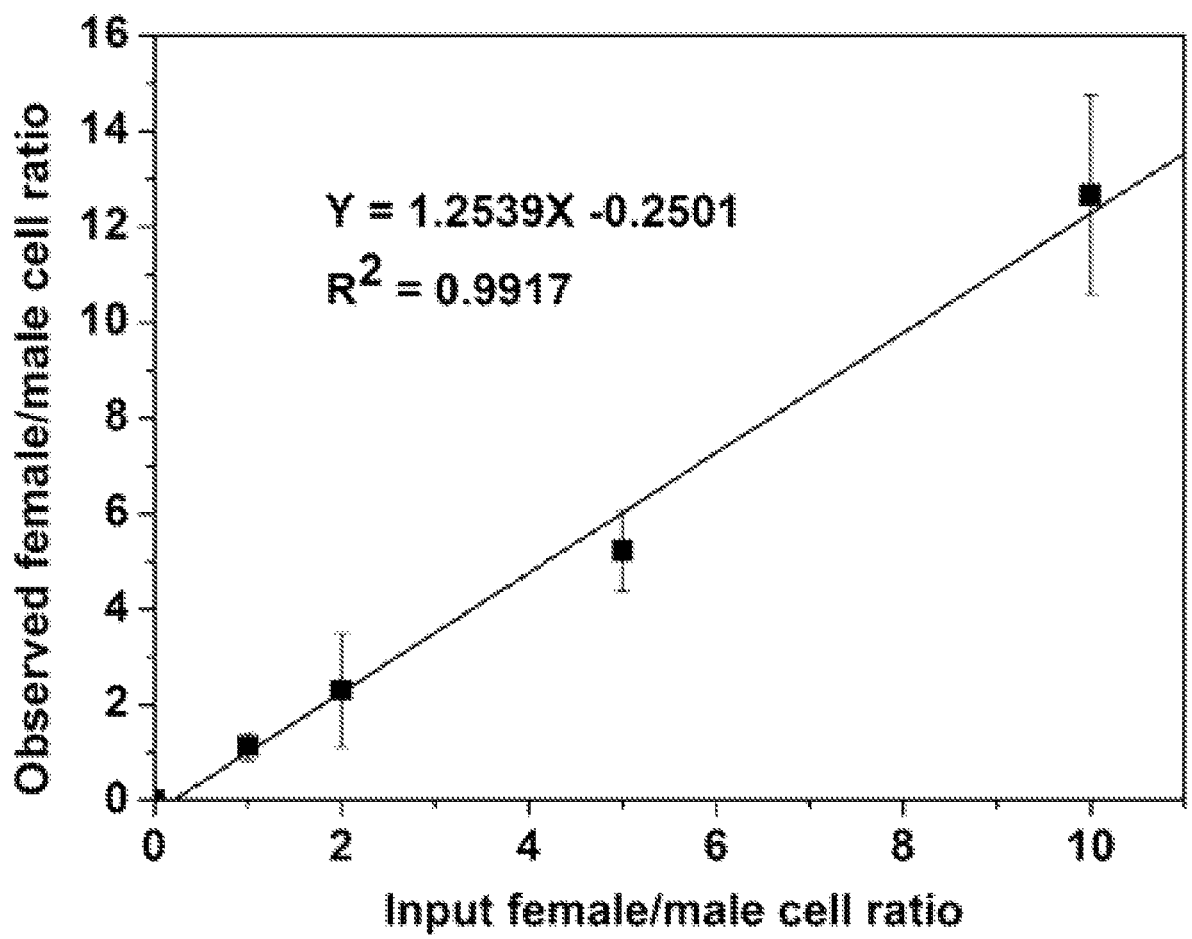
FIG. 4E shows single-cell STR typing of the GM09947 human (female) and GM09948 human (male) lymphoid cell mixtures.
Figure 5:
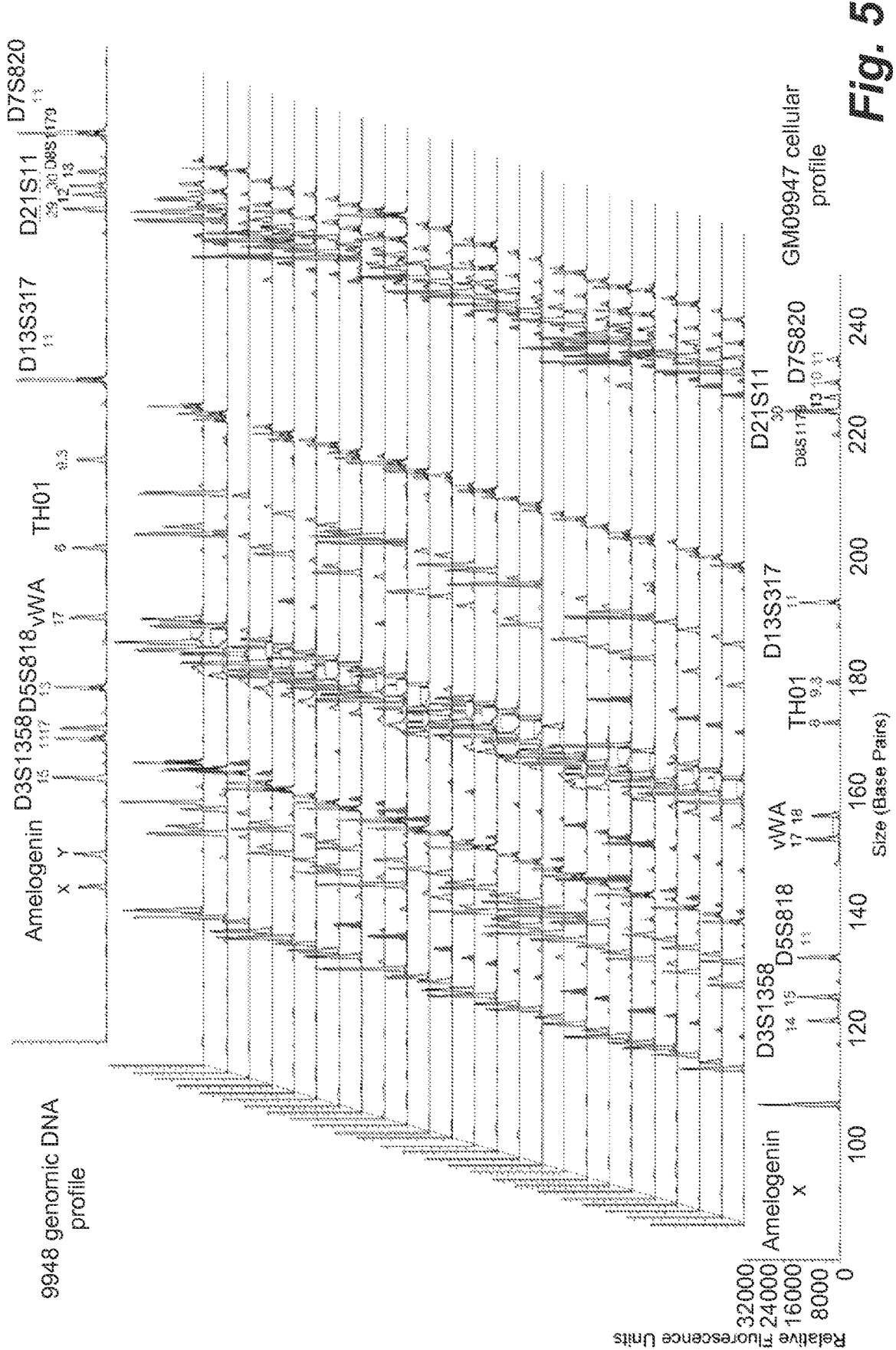
FIG. 5 shows representative STR profiles resulting from microdroplets containing GM09947 human (female) lymphoid cell, 1 copy 9948 genomic DNA and 0.9 beads per droplet on average.
Figure 6:
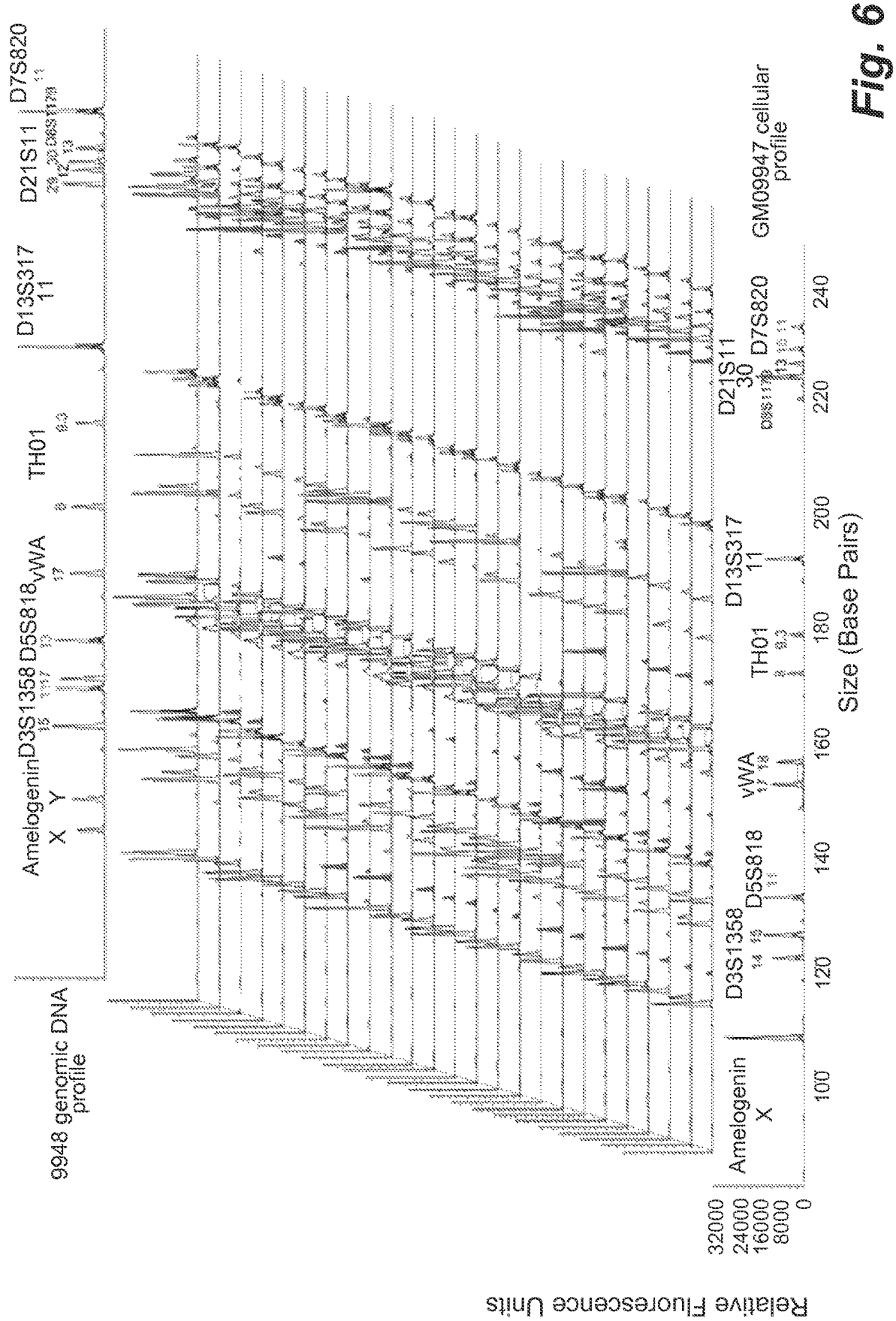
FIG. 6 shows representative STR profiles resulting from microdroplets containing 1 GM09947 human (female) lymphoid cell, 1.5 copies 9948 genomic DNA and 0.9 beads per droplet on average.
Figure 7:
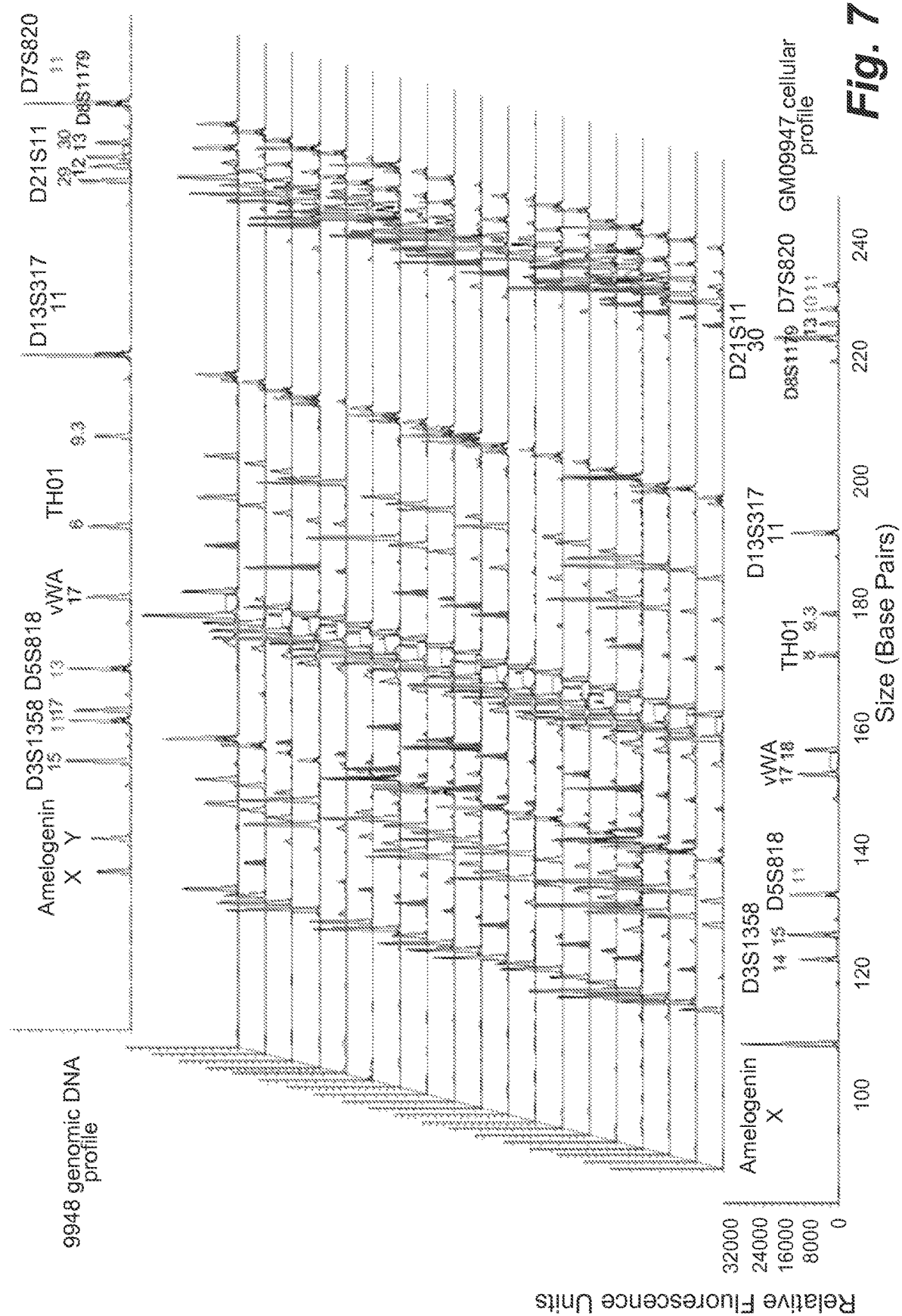
FIG. 7 shows representative STR profiles resulting from microdroplets containing 1 GM09947 human (female) lymphoid cell, 2 copies 9948 genomic DNA and 0.9 beads per droplet on average.
Figure 8:
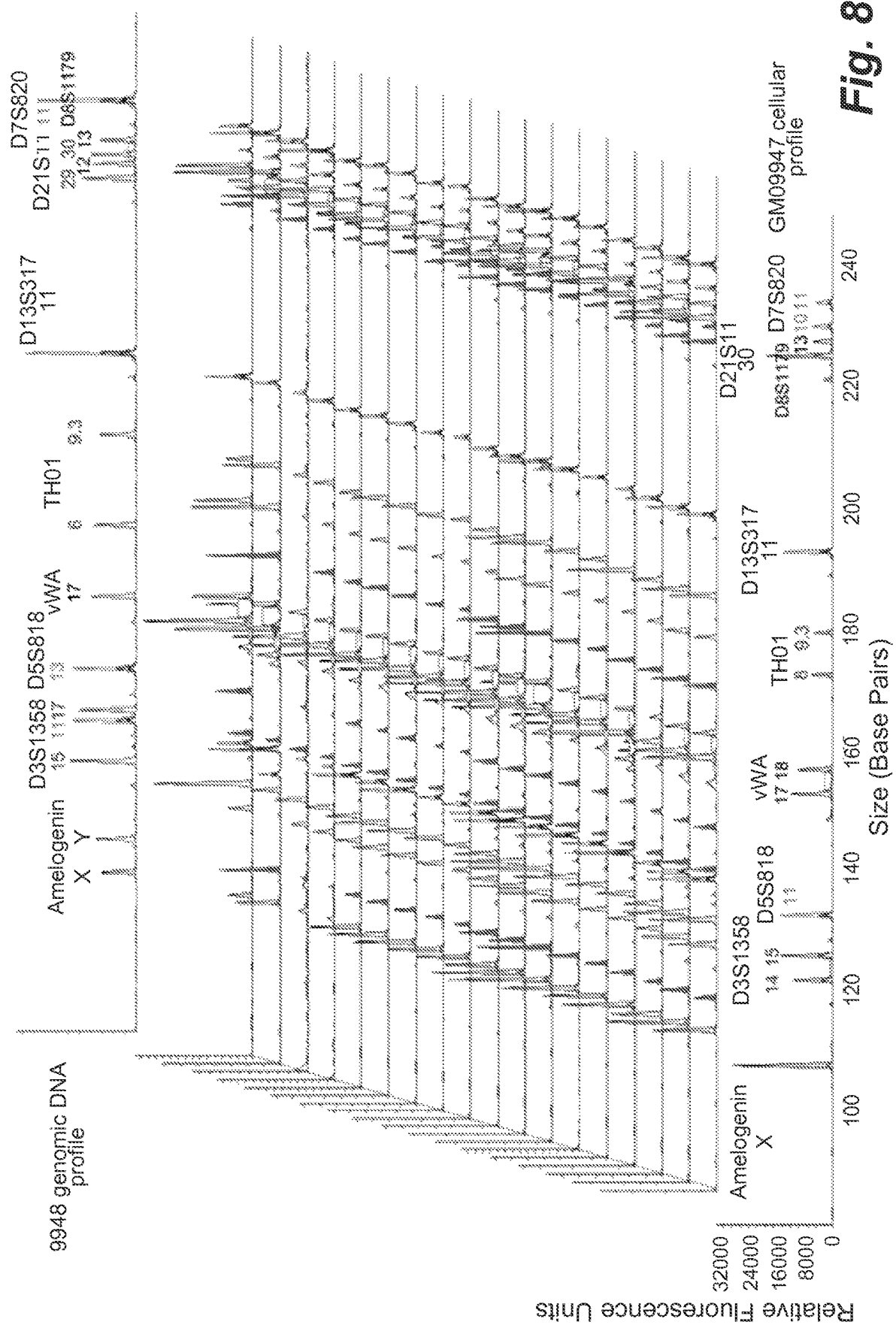
FIG. 8 shows representative STR profiles resulting from microdroplets containing 1 GM09947 human (female) lymphoid cell, 3 copies 9948 genomic DNA and 0.9 beads per droplet on average.

To detect cell mixtures with higher input ratios, more secondary PCR reactions were performed. As an example, 100 PCR reactions were conducted when the female-to-male cell ratio increased to 5:1. There were 19 positive samples which consisted of 16 STR profiles from GM09947 cells and 3 from single GM09948 cells (FIGS. 4C and 4D). In the best case, we were able to successfully identify male cells in the cell mixture when the female cells were 10 times more prevalent than the male cells using 100 PCR assays. FIG. 4E summarizes the relationship between the measured female-to-male cell number ratios and the corresponding input ratios. The good linearity ($R^2$=0.9917) indicated the high accuracy and reliability of the assay in the range of 1:1 to 10:1 cell ratios, We then used the GM09947 (female) human lymphoid cells admixed with 9948 male genomic DNA as a model system to investigate the influence of cell-free contaminating DNA on STR typing of the desired single-cell targets. In each droplet, approximately 0.9 microbeads, 1 GM09947 cell and various copy numbers (0.1, 1, 1.5, 2 and 3) of 9948 genomic DNA on average were encapsulated. The bead concentration in the secondary PCR was 0.6 beads/reaction and 70 samples were assayed in each case. Based on the concentrations, it is expected that 63% of the beads should be conjugated with STR amplicons from GM09947 cells. The probability of seeing beads with STR amplicons from 9948 DNA is dependent on the DNA concentration. Except at 0.1 copies/droplet (59%), nearly all beads should have products from 9948 DNA, though the number of STR loci on these beads will be variable due to the stochastic distribution of the various DNA template fragments within the droplets. Mixed genotypes from both GM09947 cells and 9948 genomic DNA (FIGS. 5 and 6-8) as well as partial genotypes from 9948 genomic DNA were obtained. In FIG. 5, under the statistically dilute conditions it is expected that approximately 63% of the beads will have all GM09947 cellular STR products and 95% of the beads will have at least one of the 9948 DNA-specific STR products. In total 70 samples were tested in secondary PCR using 0.6 beads per reaction (predicting 0.6×0.63=0.378 GM09947-cell-DNA-positive beads per reaction) on average. There were 23 positive analyses, which was consistent with the theoretical value of 31% predicted by the Poisson distribution. In all cases, 30 cycles of emulsion PCR and 25 cycles of secondary PCR were performed. Red filled peaks indicate 9948 DNA-specific peaks which appear randomly By comparing with the known STR profiles of GM09947 cells and 9948 genomic DNA, we found that 6 allele peaks (Amelogenin-X, D3S1358-17, D5S818-13, D21S11-29 and D8S1179-12) were specific for 9948 genomic DNA and distinct from GM09947 cellular DNA profiles. We calculated the percentage of the STR profiles that were composed of all 13 allele peaks from GM09947 cells and had a given number (0, 1, 2, 3, 4, 5 or 6) of 9948-DNA-specific peaks, and plotted the percentage as a function of the number of 9948-DNA-specific peaks in FIG. 9. The percentage of profiles containing all GM09947 cellular peaks and a certain number (0, 1, 2, 3, 4, 5 or 6) of 9948-DNA-specific peaks in profiles containing all GM09947 cellular peaks (any profile containing all peaks from a GM09947 cell) is plotted vs. the number of 9948-DNA-specific peaks as a function cell-free DNA concentration. 9948 genomic DNA was encapsulated in microdroplets together with GM09947 human (female) lymphoid cells at the frequency of 0.1, 1, 1.5, 2 and 3 copies DNA, 1 cell and 0.9 beads per droplet on average. Under the statistically dilute conditions it is expected that approximately 63% beads will have all STR products from GM09947 cells, and 76%, 95%, 98.89%, 99.75% and 99.99% beads will have at least one of the 9948 DNA-specific STR products, respectively. In total 70 samples were tested in secondary PCR using 0.6 beads per reaction on average. In all cases, 30 cycles of emulsion PCR and 25 cycles of secondary PCR were performed, At low background DNA concentration (0.1 copies/droplet), 82% of the profiles had only GM09947 cellular peaks detected and 18% of the profiles had only one additional 9948-DNA-specifc peak. Thus, at this relative concentration the cell-free DNA did not significantly affect the data interpretation. When the input 9948 DNA was increased to 1 copy/droplet, no pure GM09947-cell profiles were obtained, but the percentage of profiles containing one more 9948-DNA-specific peak was only 30% (FIG. 5). The background DNA peaks could be easily excluded from the cellular peaks by comparing these STR profiles. A peak can be assigned as background DNA if it is not observed in all profiles. The percentages of profiles containing more 9948-DNA-specific peaks rose with increasing background 9948 DNA loading. At 1.5 copies/droplet, most profiles had only four 9948-DNA-specific peaks plus the GM09947-cell peaks, but still 8% profiles contained only one additional 9948-DNA-specific peak (FIG. 6). At 2 copies/droplet, the highest percentage (32%) of profiles had six 9948-DNA-specifc peaks, and profiles containing two additional 9948-DNA-specific peaks still could be detected (5.3%) (FIG. 7). Even when the DNA concentration was increased to 3 copies/droplet, 5.6% of the profiles additionally contained four 9948-DNA-specific peaks. Nevertheless, all six 9948-DNA-specific peaks appeared in the vast majority (78%) of profiles (FIG. 8).

In principle, the cellular STR profile could be deduced from these cell/DNA mixture experiments when sufficient secondary PCR reactions are carried out. Therefore, the droplet microfluidic technique provides a valuable method that statistically dilutes the extracellular DNA fragments together with the target cells, leading to minimal interference with each individual droplet PCR reaction and easy interpretation of STR genotypes. We can conclude from the data that it is feasible to type single cells with contaminating DNA at or below 2 copies of contaminating genomic DNA/ target cell. This benefit should also apply to forensic samples contaminated with PCR inhibitors (e.g. environmental elements or natural contaminants). In traditional bulk solution PCR any contaminant affects the entire PCR reaction, whereas in emulsion PCR the contaminant only impacts the microdroplet wherein it is encapsulated.

Our droplet-microfluidics based STR typing technology provides several technological advantages over conventional forensic genetic methods for single-cell analysis. First, it avoids the complex and expensive cell separation instrumentation in other single-cell assays such as laser capture microdissection, fluorescence-activated cell sorting and micromanipulation All processes can be accomplished in standard laboratory setup, and the microfluidic droplet generators are disposable and affordable. Second, multiple steps, from cell isolation to cell lysis and DNA release for subsequent PCR amplification, are performed in a single droplet reactor for an individual cell, substantially improving the efficiency of sample handling. Another key benefit of microdroplets is that their nanoscale reaction volume significantly increases the concentration of starting materials, thereby improving the single-cell PCR efficiency. Compared to other droplet PCR assays, the method disclosed herein enhances the level of multiplexing to nine by using the 5 functionalized beads. The relatively large surface area of the beads provides sufficient amplicon-binding spaces for the 9 STR targets without unbalanced amplification for each locus. Moreover, although the overall experimental analysis time (~22 h including 3.5 h working time and 18.5 h waiting time) is not dramatically improved, the complete resolution of the cell mixtures avoids complicated mixture interpretation, it is also worth noting that frozen cells can be processed by the method disclosed herein and yield comparable genotypes to fresh cells, facilitating the single-cell STR analysis of stored samples. The power of the method will be further enhanced by expanding the STR multiplex to the full 13 CODIS loci for standard casework analysis.

CONCLUSION

In summary, we have demonstrated a novel approach for multiplex STR typing at the single-cell level using agarose droplets generated with a simple PDMS/glass microfluidic device. Taking advantage of droplet microfluidics, individual cells were efficiently encapsulated in nanoliter agarose droplets which subsequently served as the reactors for emulsion PCR assays. A large number of single-cell PCR reactions were implemented in a standard PCR tube in a highly parallel manner, substantially increasing the throughput of the analysis an important step to produce statistically valid results when performing single-cell studies. The expected profiles of 9 STR loci were successfully detected from both pure and mixed single-cell samples (GM09947 and GM0998 human lymphoid cells) with high single-genome integrity. Distinct cells could be efficiently discriminated in mixture at a 10:1 background ratio. STR profile interpretation was also effective in the presence of significant background cell-free DNA. This method has the potential to be immediately used in common forensic laboratories since no sophisticated equipment is involved in the protocol disclosed herein and the final data appears in a familiar conventional STR format. The improvements in sensitivity and selectivity should lead to more accurate and reliable results from samples containing low amounts of cells and/or mixed cells such as samples left on touched surfaces and sexual assault crimes. Future work will extend this method to analyzing real-world mixed and dilute samples to identify multiple suspects from low-abundance materials.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for genetic profiling of multiple short tandem repeat DNA sequences from individual single cells without allelic drop-out, the method comprising:
   forming polymer gel droplets containing statistically dilute primer-functionalized beads and cells, wherein the cells are from a complex biological sample comprising a mixture of cells from multiple human individuals and wherein the forming comprises selecting a concentration of the cells, primer-functionalized beads and polymer gel droplets such that no more than one single cell is encapsulated with a primer-functionalized bead in a polymer gel droplet;
   isolating DNA sequences from each of the single cells in each of the polymer gel droplets;
   performing multiplex amplification of the multiple short tandem repeat DNA sequences from each of the single cells in each of the polymer gel droplets, wherein the multiplex amplification comprises transferring replicas of the multiple short tandem repeat DNA sequences from the single cell in each polymer gel droplet onto the primer-functionalized bead in the polymer gel droplet;
   isolating the beads from the polymer gel droplets;
   statistically diluting the isolated beads for a secondary amplification;
   performing multiplex amplification of the multiple short tandem repeat DNA sequences from a single cell on each individual bead;
   separately determining the tandem repeat length of each of the multiple short tandem repeat DNA sequences from each of the single cells;
   identifying the multiple short tandem repeat DNA sequences to provide a short tandem repeat DNA profile of each of the single cells; and
   comparing the short tandem repeat DNA profile of each single cell to a known DNA profile for human forensic identification.

2. The method of claim 1, wherein performing the amplification comprises performing PCR.

3. The method of claim 1, wherein the length is determined by size-based separation.

4. The method of claim 1, wherein determining the length comprises performing capillary electrophoresis.

5. The method of claim 1, wherein the DNA sequences are genomic DNA sequences.

6. The method of claim 1, wherein the identifying comprises sequencing the DNA sequences.

7. The method of claim 1, wherein the performing the multiplex amplification comprises performing emulsion oil PCR amplification of the multiple short tandem repeat DNA sequences.

8. The method of claim 1, wherein the polymer gel droplets are microfluidic droplets.

9. The method of claim 1, wherein the short tandem repeat DNA profile comprises a short tandem repeat genotype of the single cell.

10. The method of claim 1, wherein the polymer gel droplet comprises an aqueous polymer gel.

11. The method of claim 10, wherein the aqueous polymer gel is an agarose gel.

* * * * *